(12) United States Patent
Jamieson et al.

(10) Patent No.: US 7,816,088 B2
(45) Date of Patent: Oct. 19, 2010

(54) IDENTIFICATION, ISOLATION AND ELIMINATION OF CANCER STEM CELLS

(75) Inventors: Catriona Helen M. Jamieson, La Jolla, CA (US); Laurie Ailles, Palo Alto, CA (US); Irving L. Weissman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 725 days.

(21) Appl. No.: 10/579,540

(22) PCT Filed: Dec. 6, 2004

(86) PCT No.: PCT/US2004/040879

§ 371 (c)(1),
(2), (4) Date: Mar. 9, 2007

(87) PCT Pub. No.: WO2005/057172

PCT Pub. Date: Jun. 23, 2005

(65) Prior Publication Data

US 2008/0020407 A1 Jan. 24, 2008

Related U.S. Application Data

(60) Provisional application No. 60/527,411, filed on Dec. 5, 2003, provisional application No. 60/580,176, filed on Jun. 15, 2004.

(51) Int. Cl.
*G01N 33/53* (2006.01)
*C12N 5/08* (2006.01)

(52) U.S. Cl. .................................. 435/7.1; 435/372

(58) Field of Classification Search .................. None
See application file for complete search history.

(56) References Cited

U.S. PATENT DOCUMENTS

| | | | |
|---|---|---|---|
| 6,465,247 | B1 | 10/2002 | Weissman et al. |
| 6,761,883 | B2 | 7/2004 | Weissman et al. |
| 6,908,763 | B1 | 6/2005 | Akashi et al. |
| 7,217,568 | B2 | 5/2007 | Jamieson et al. |
| 2003/0119080 | A1 | 6/2003 | Mangano |
| 2004/0171559 | A1 | 9/2004 | Weissman et al. |
| 2007/0238127 | A1 | 10/2007 | Jamieson et al. |

FOREIGN PATENT DOCUMENTS

| | | |
|---|---|---|
| WO | WO9910478 A1 | 3/1999 |
| WO | WO 01/92877 A2 | 12/2001 |

OTHER PUBLICATIONS

Dührsen, U., et al., "Self-renewal and differentiation of stem cells in a bipotential murine leukemia: an in vitro model for differentiation therapy," (1994) *Blood*, 83(9):2627-2636.
Jamieson, C., et al,, "Expression by highly purified chronic myelogenous leukemic hematopoietic stem cells and myeloid progenitors pre and post-imatinib therapy," (2003) *Blood*, 102(11:Abstract #1519.
Kussick, S., et al., "Acute myeloid leukemia bearing the Flt3 internal tandem duplication has a unique immunophenotype which enables its identification by flow cytometry," (2002) *Blood*, 100(11):Abstract #737.
Petzer, A., et al., "Characterization of primitive subpopulations of normal and leukemic cells present in the blood of patients with newly diagnosed as well as established chornic myeloid leukemia," (1996) *Blood*, 88(6):2162-2171.
Testa, U., et al., "Human acute stem cell leukemia with multilineage differentiation potential via cascade activation of growth factor receptors," (2002) *Blood*, 99(12):4634-4637.
Akashi et al., "A clonogenic common myeloid progenitor that gives rise to all myeloid lineages", Nature, 2000, 404 (6774):193-7.
Kondo et al., "Identification of clonogenic common lymphoid progenitors in mouse bone marrow", Cell, 1997, 91 (5):661-72.
Kondo et al., "Biology of hematopoietic stem cells and progenitors: implications for clinical application" Annu. Rev. Immunol, , 2003, 21:759-806.
Onida et al., "Prognostic factors and scoring systems in chronic myelomonocytic leukemia: a retrospective analysis of 213 patients"Blood, , 2002, 99(3):840-849.

*Primary Examiner*—Michail A Belyavskyi
(74) *Attorney, Agent, or Firm*—Bozicevic, Field & Francis LLP; Pamela J. Sherwood

(57) ABSTRACT

Isolated populations of leukemic stem cells are provided. The cells are useful for experimental evaluation, and as a source of lineage and cell specific products, and as targets for the discovery of factors or molecules that can affect them. Detection of leukemic stem cells is useful in predicting disease progression, relapse, and development of drug resistance. Proliferation of LSC may be inhibited through interfering with activation of the bcatenin pathway. Methods are provided for the clinical staging of pre-leukemia and leukemias by differential analysis of hematologic samples for the distribution of one or more hematopoietic stem or progenitor cell subsets.

14 Claims, 20 Drawing Sheets

FIG. 1
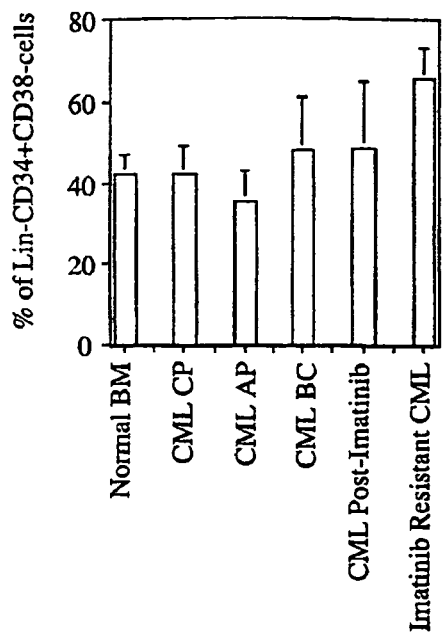
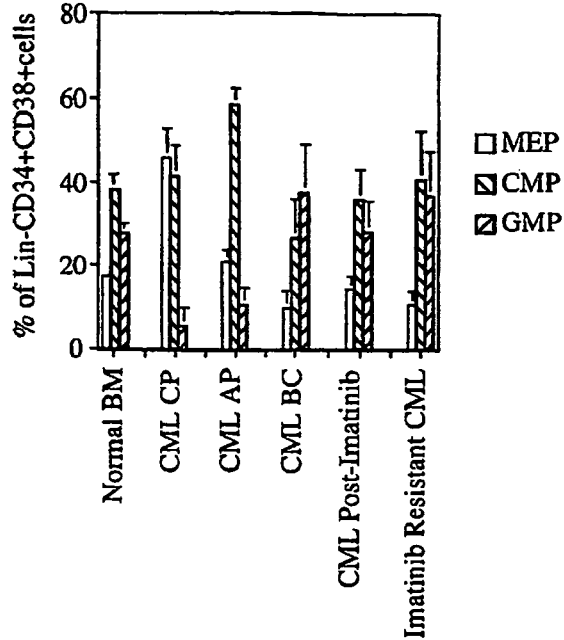
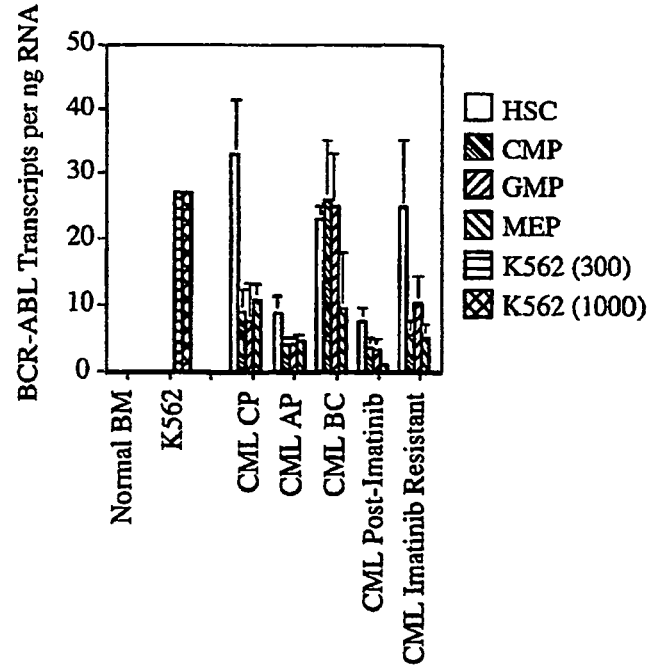

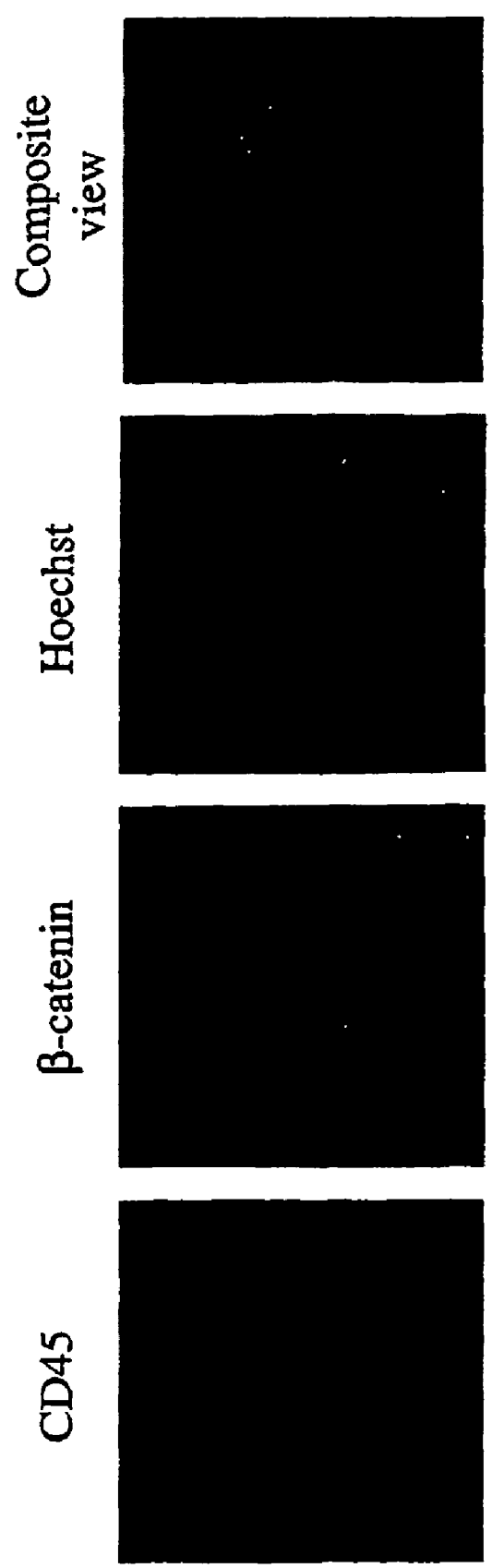

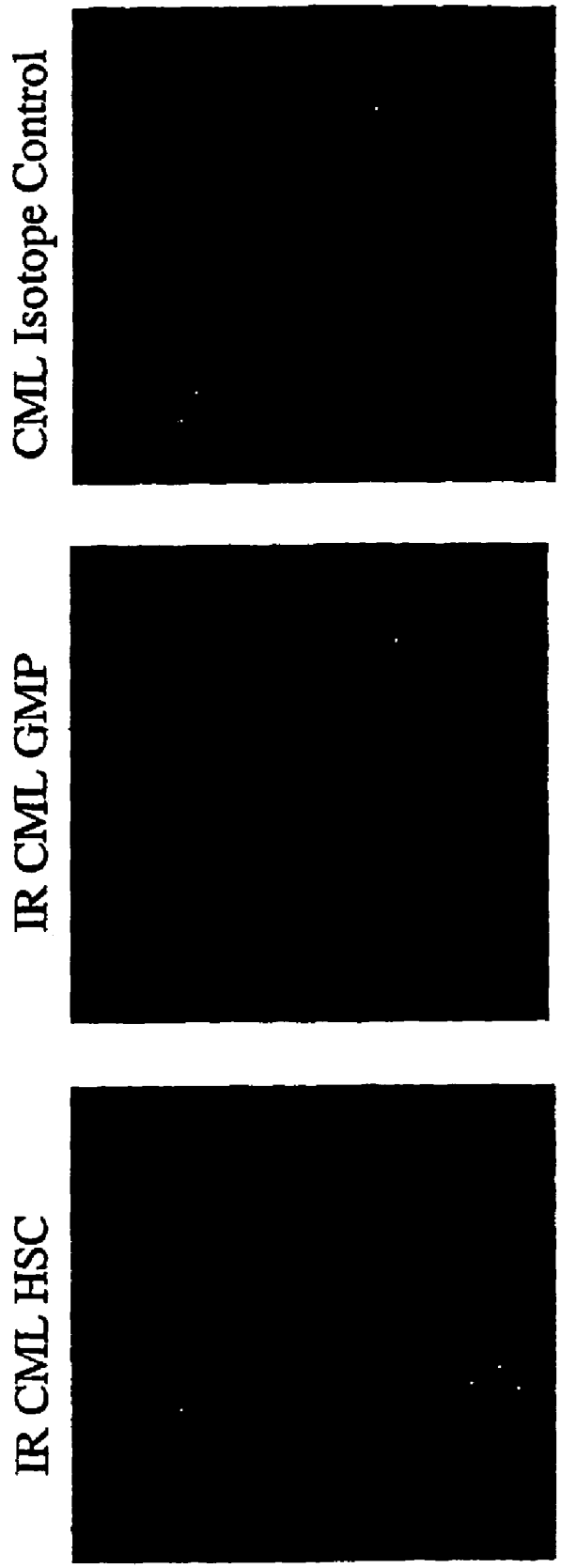

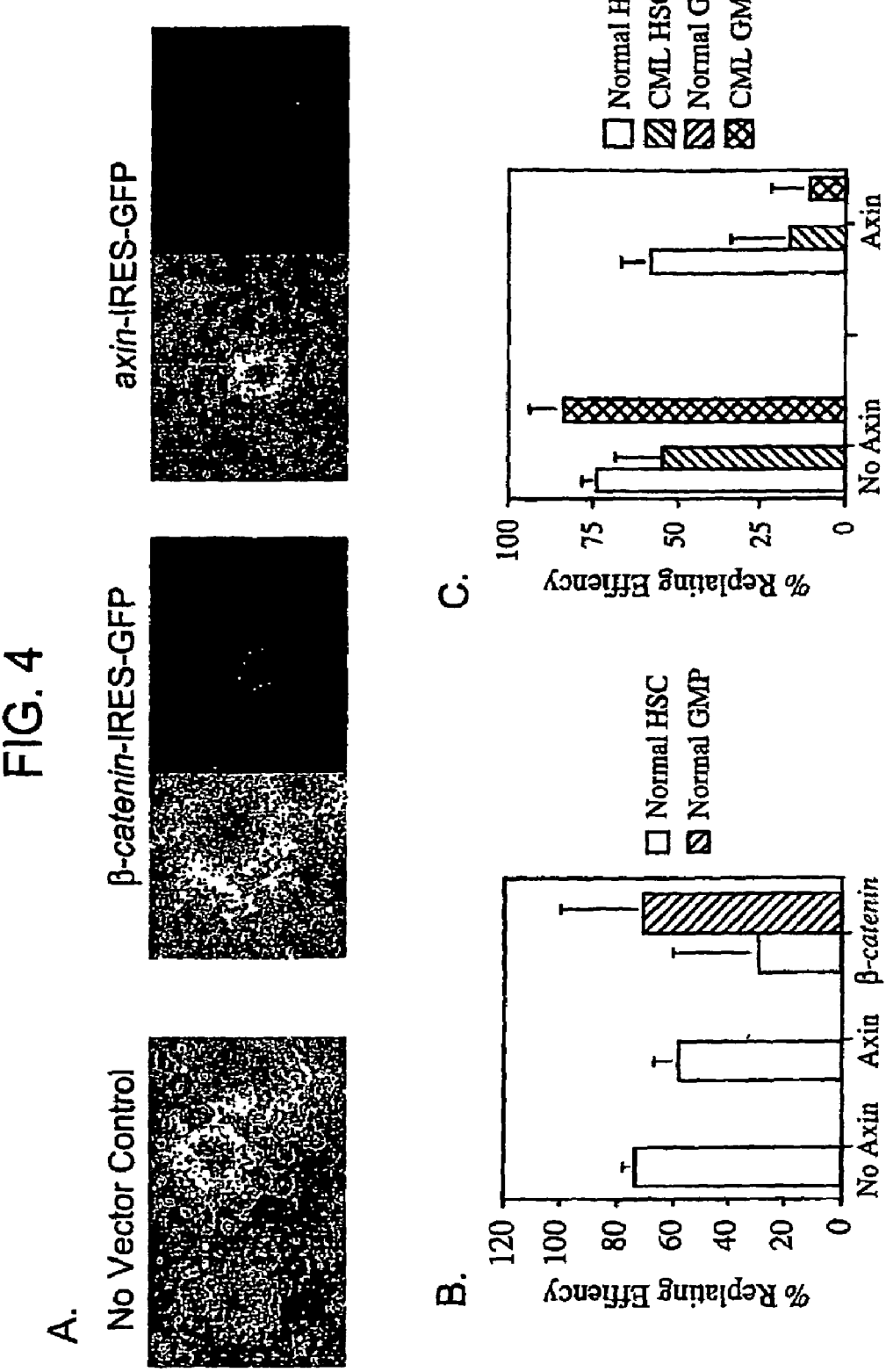

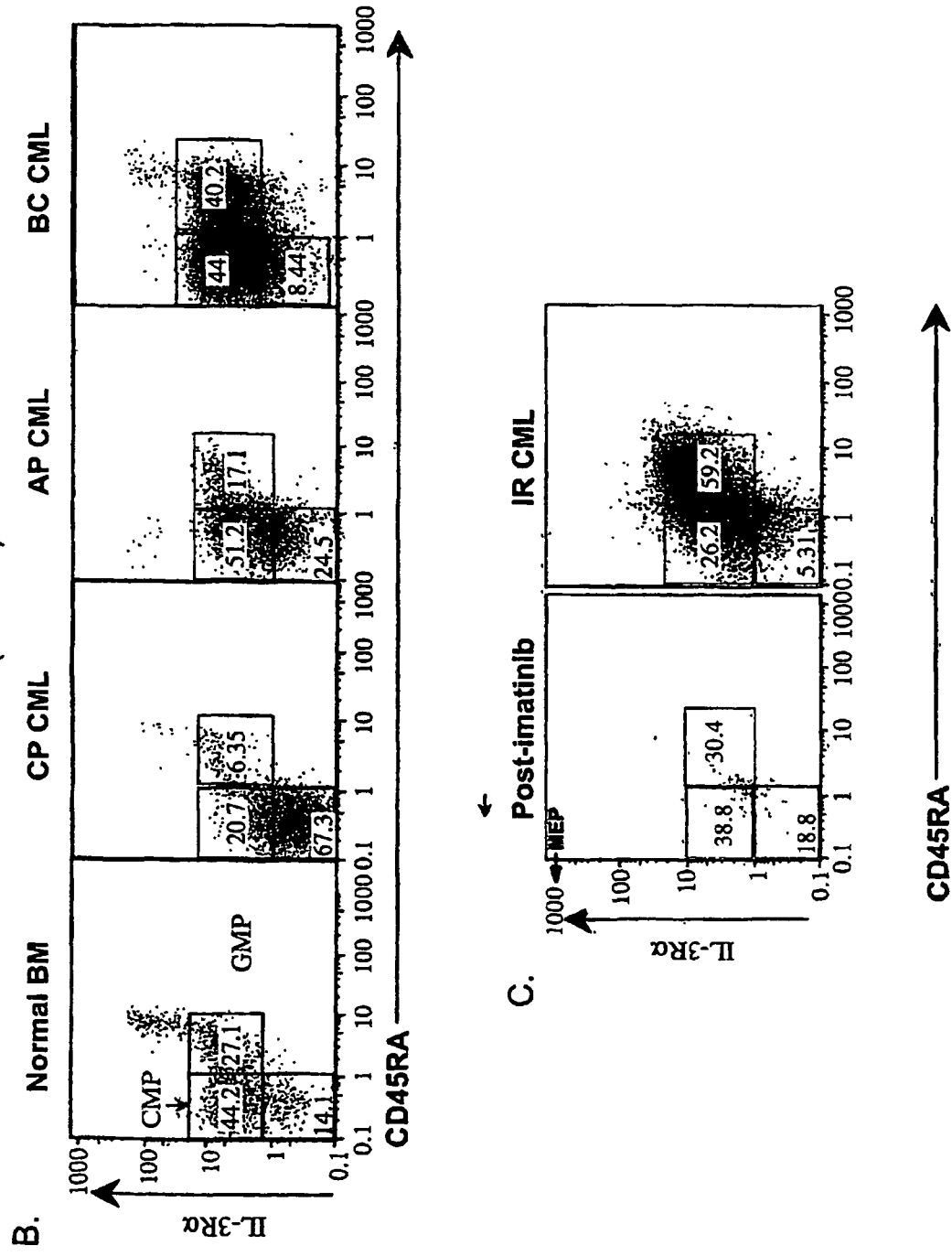

FIG. 8

FIG. 14
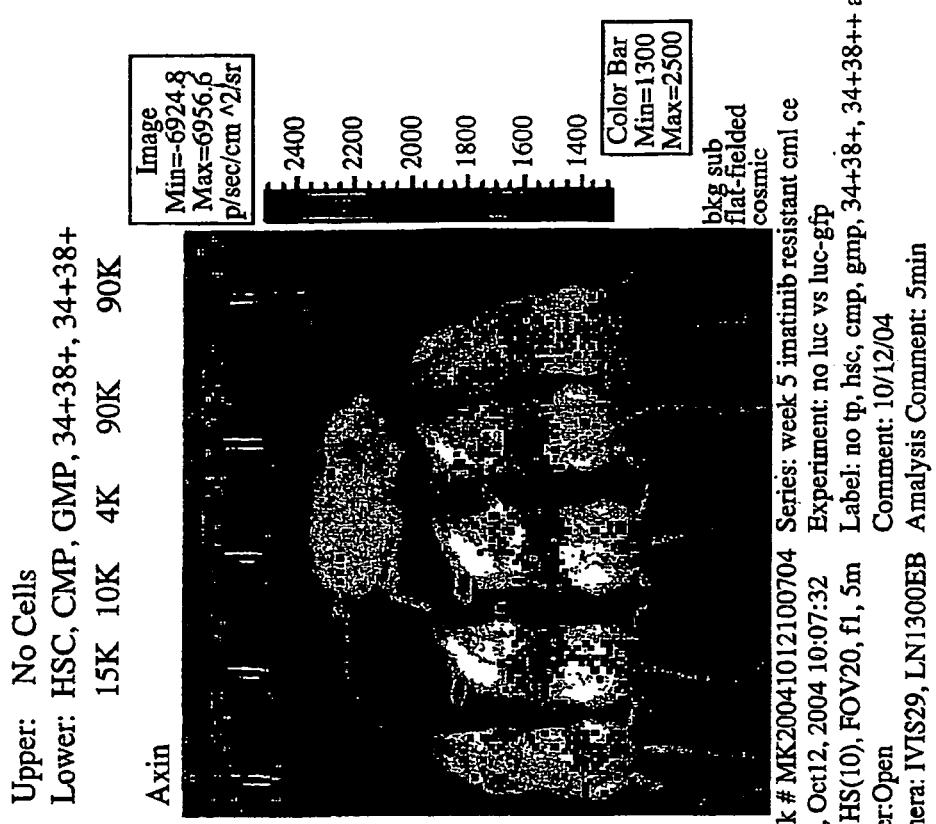
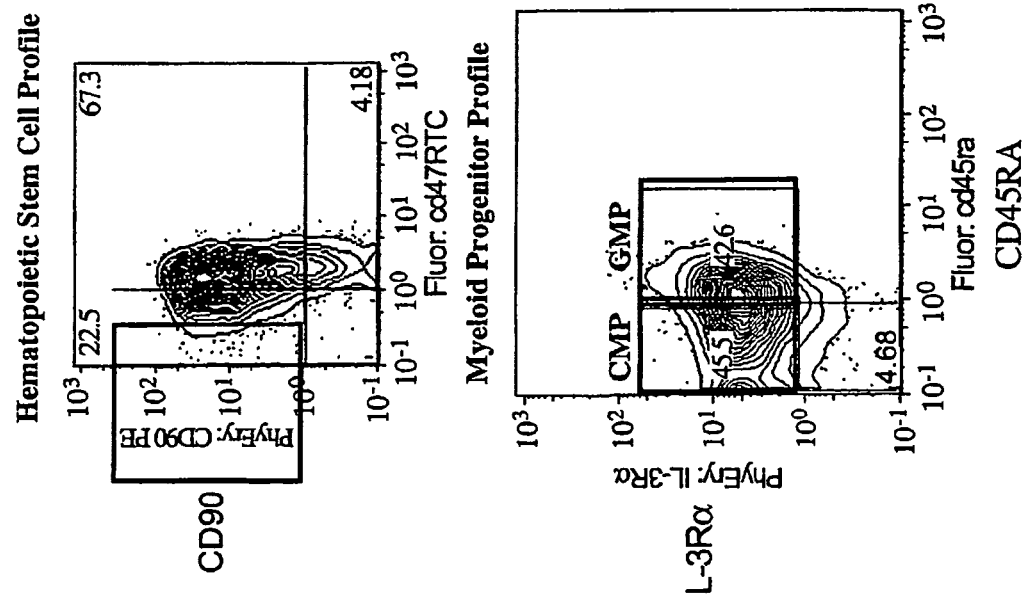

SEQUENCE LISTING

```
<160> NUMBER OF SEQ ID NOS: 14

<210> SEQ ID NO 1
<211> LENGTH: 9
<212> TYPE: DNA
<213> ORGANISM: homo sapiens

<400> SEQUENCE: 1 cctttgatt                                                                9

<210> SEQ ID NO 2
<211> LENGTH: 9
<212> TYPE: DNA
<213> ORGANISM: homo sapiens

<400> SEQUENCE: 2 gctttgatc                                                                9

<210> SEQ ID NO 3
<211> LENGTH: 9
<212> TYPE: DNA
<213> ORGANISM: homo sapiens

<400> SEQUENCE: 3 cctttgatc                                                                9

<210> SEQ ID NO 4
<211> LENGTH: 9
<212> TYPE: DNA
<213> ORGANISM: homo sapiens

<400> SEQUENCE: 4 cctttggcc                                                                9

<210> SEQ ID NO 5
<211> LENGTH: 11
<212> TYPE: DNA
<213> ORGANISM: homo sapiens

<400> SEQUENCE: 5
```

```
gctttgatct t                                                    11

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
aatcagctgg cctggtttga                                           20

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ggccaatcac aatgcaagtt c                                         21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ccagagcatc ttgcatccaa a                                         21

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
ttgcgcatga caggcaaat                                            19

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
cgtcttgctc gagatgtgat g                                         21

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
tttatagccc cccttgagca c                                         21

<210> SEQ ID NO 12
<211> LENGTH: 9
<212> TYPE: DNA
```

```
<213> ORGANISM: Artificial Sequence
<220> FEATURE:
<223> OTHER INFORMATION: binding motif sequence
<220> FEATURE:
<221> NAME/KEY: misc_feature
<222> LOCATION: (1)...(1)
<223> OTHER INFORMATION: n = G or C

<400> SEQUENCE: 12 nctttgrty                                                                      9

<210> SEQ ID NO 13
<211> LENGTH: 10
<212> TYPE: DNA
<213> ORGANISM: homo sapiens

<400> SEQUENCE: 13
gatcaaaggg                                                                    10

<210> SEQ ID NO 14
<211> LENGTH: 9
<212> TYPE: DNA
<213> ORGANISM: Artificial Sequence
<220> FEATURE:
<223> OTHER INFORMATION: binding motif sequence
<220> FEATURE:
<221> NAME/KEY: misc_feature
<222> LOCATION: (9)...(9)
<223> OTHER INFORMATION: n = G or C

<400> SEQUENCE: 14 raycaaagn                                                                      9
```

IDENTIFICATION, ISOLATION AND ELIMINATION OF CANCER STEM CELLS

FEDERALLY-SPONSORED RESEARCH OR DEVELOPMENT

This invention was made with Government support under contract CA086017 awarded by the National Institutes of Health. The Government has certain rights in this invention.

BACKGROUND OF THE INVENTION

Leukemia is a malignant disease of the blood-forming organs, which involves the distorted proliferation and development of white blood cells in bone marrow and blood. Leukemias are usually classified as myelogenous or lymphocytic, according to the types of cells that are involved. Within these groups, there are chronic and acute conditions, which vary in duration and character. Leukemias tend to have age specificity, for example acute lymphoid leukemia generally occurs in young children, while acute myelogenous leukemia is found principally in young adults.

The ability to isolate purified populations of hematopoietic stem cells and myeloid progenitors based on characteristic cell surface (phenotypic) markers has made it possible to identify genes involved in hematopoietic stem cell self-renewal. Normal hematopoietic stem cells, unlike committed hematopoietic progenitors, have the capacity to divide and make identical progeny without undergoing differentiation i.e. self-renewal. Deregulation of self-renewal pathways, which are normally tightly regulated in hematopoietic stem cells, has recently been recognized as an important step in leukemic progression.

Chronic myelogenous leukemia (CML) is a disease having distinct clinical and pathological features. The cause of CML is a specific chromosomal translocation between human chromosomes 9 and 22, resulting in a product commonly referred to as the Philadelphia chromosome. The gene for the tyrosine kinase c-abl resides on the distal arm of human chromosome 9, while the gene for c-bcr resides on human chromosome 22. The translocation places the promoter distal three exons of ABL, including those elements that encode the tyrosine kinase domain, downstream of either the first or second exon of BCR. This chimeric gene, BCR-ABL, encodes a fusion protein often referred to as $p185^{bcr-abl}$ or $p210^{bcr-abl}$, depending upon the inclusion of the second exon of BCR. $p185^{bcr-abl}$ causes acute leukemia, typically lymphoblastic; $p210^{bcr-abl}$ usually causes CML which may progress to myeloid or lymphoid blast crisis.

Treatment of leukemias has traditionally relied on chemotherapy using anti-neoplastic agents, radiation therapy, corticosteroid therapy and immunotherapy, which may be performed in combination with transplantation of hematopoietic stem cells. Different therapies are utilized depending upon the type of leukemia being treated.

Recently a new class of antiproliferative agents called signal transduction inhibitors has been introduced, which interferes with the pathways that signal the growth of tumor cells. Gleevec (imatinib mesylate) is targeted to the constitutively active abnormal tyrosine kinase created by the Philadelphia chromosome. Imatinib is also an inhibitor of the receptor tyrosine kinases for platelet-derived growth factor (PDGF) and stem cell factor (SCF), c-kit, and inhibits PDGF- and SCF-mediated cellular events.

However, despite the effectiveness of imatinib in inducing both hematologic and cytogenetic remissions in the majority of chronic phase (CP) CML patients, some patients progress, in part as a result of amplification of BCR-ABL and point mutations in the binding site for imatinib on the abl tyrosine kinase active site of P210. In addition, patients who become resistant to Imatinib and develop accelerated phase (AP) or blast crisis (BC) frequently demonstrate clonal evolution with trisomy 8 and other chromosomal abnormalities suggesting that activation of other oncogenes may contribute to disease progression. Finally, the role of BCR-ABL amplification and additional oncogene activation in HSCs or more committed progenitors with increased proliferative and self-renewal capacity, as a result of aberrant overexpression of hematopoietic stem cell self-renewal genes such as β-catenin, is of great interest.

In another myeloid leukemia, t(8;21) acute myelogenous leukemia, marrow from patients in complete remission contains apparently normal hematopoietic stem cells that produce AML1-ETO transcripts, and their presence during remission implies that such hematopoietic stem cells are pre-leukemic rather than leukemic cells (these transcripts participate in the development of acute myeloid leukemia; AML1-ETO is formed by the fusion of part of the AML1 gene on chromosome 8 with part of the ETO gene on chromosome 21). Similarly, genomic BCR-ABL persists in the marrow of some CML patients who are in a sustained complete cytogenetic remission, and has been detected at very low levels in the leukocytes of healthy individuals, which suggests that preleukemic hematopoietic stem cells or more differentiated progenitor cells need additional mutations for progression to overt leukemia.

Bone marrow HSCs are functionally defined by their unique capacity to self-renew and to differentiate to produce all mature blood cell types. In general, the process of development from pluripotent progenitors to mature cells with specific functions involves the progressive loss of developmental potential to other lineages. A hierarchy has emerged in which each successive developmental stage loses the potential to become a specific cell type or class of cells. This stepwise developmental process has been considered linear in the sense that once a cell has made a developmental choice it cannot revert. The earliest known lymphoid-restricted cell in adult mouse bone marrow is the common lymphocyte progenitor (CLP), and the earliest known myeloid-restricted cell is the common myeloid progenitor (CMP). Importantly, these cell populations possess an extremely high level of lineage fidelity in in vitro and in vivo developmental assays. A complete description of these cell subsets may be found in Akashi et al. (2000) Nature 404(6774):193, U.S. Pat. No. 6,465,247; and published application U.S. Ser. No. 09/956,279 (common myeloid progenitor); Kondo et al. (1997) Cell 91(5):661-7, and International application WO99/10478 (common lymphoid progenitor); and is reviewed by Kondo et al. (2003) Annu Rev Immunol. 21:759-806, each of which is herein specifically incorporated by reference.

CD34+ cells harbor virtually all in vitro clonogenic potential; however, the CD34+ population is heterogeneous. Only a small fraction (1-10%) of CD34+ cells that do not express mature lineage markers (Lin⁻, including the markers CD3, CD4, CD8, CD19, CD20, CD56, CD11b, CD14, and CD15) have multilineage (lymphoid and myeloid) developmental potential. The majority of CD34+ cells (90-99%) coexpress the CD38 antigen, and this subset contains most of the lineage-restricted progenitors.

SUMMARY OF THE INVENTION

Cancer stem cells are identified, including a leukemic stem cell (LSC). These cells are responsible for disease progression, and for resistance to chemotherapeutic drugs. LSC have a phenotype similar to that of a hematopoietic progenitor cell, which differs from the normal progenitor cells in that the leukemia stem cell has acquired an activated β-catenin pathway. As a result, the LSC have acquired the proliferative and self-renewal capacity that is normally restricted to hematopoietic stem cells. In CML, the LSC responsible for disease progression are phenotypically similar to a granulocyte/macrophage progenitor cell.

In another embodiment of the invention, methods are provided for the clinical staging of pre-leukemia and leukemias, particularly chronic leukemias, e.g. chronic myelogenous leukemia (CML); chronic myelomonocytic leukemia, etc. by analysis of the presence of hematopoietic stem or progenitor cells, which cells may include LSC. Staging is useful for prognosis and treatment. In such methods, hematologic samples, e.g. blood, lymph, bone marrow aspirate, etc. can be differentially analyzed for the presence of one or more hematopoietic stem or progenitor cells, which may include LSC, hematopoietic stem cells; myeloid progenitors; common lymphoid progenitors; megakaryocyte progenitors; etc., wherein the distribution of progenitor cells in the $CD34^+$ compartment of the blood is diagnostic of the stage of the leukemia. A utility of particular interest is the early diagnosis of acceleration of patients with pre-leukemic or chronic leukemias.

In another embodiment of the invention, compositions of isolated LSC are provided. The cells are useful for experimental evaluation, and as a source of lineage and cell specific products, including mRNA species useful in identifying genes specifically expressed in these cells, and as targets for the discovery of factors or molecules that can affect them. LSC may be used, for example, in a method of screening a compound for an effect on the cells. This involves combining the compound with the cell population of the invention, and then determining any modulatory effect resulting from the compound. This may include examination of the cells for toxicity, metabolic change, or an effect on cell function. The phenotype of LSC described herein provides a means of predicting disease progression, relapse, and development of drug resistance. Such methods include determination of activated β-catenin levels in a patient sample, e.g. a blood sample; enumeration of the granulocyte/macrophage progenitors present in a patient sample, and the like.

In another embodiment of the invention, methods are provided for inhibition of LSC proliferation, by inhibiting β-catenin activation. Various Wnt inhibitors are shown to inhibit the proliferation of LSC.

BRIEF DESCRIPTION OF THE DRAWINGS

FIG. 1. A) The proportion of hematopoietic stem cells ($CD90^+$) within the $CD34^+CD38^-Lin^-$ population of normal (n=11) versus chronic phase (n=5), accelerated phase (n=6), blast crisis (n=4), post-imatinib (n=6) and imatinib resistant (n=4) bone marrow. B) The percentage of individual myeloid progenitor populations including common myeloid progenitors, granulocyte/macrophage progenitors and megakaryocyte/erythroid progenitors, expressed as percent of the $CD34^+CD38^+Lin^-$ fraction of the same samples. Statistics were performed with Excel software and the Student's unpaired two-tailed T-test. C) The average BCR-ABL transcripts per nanogram of RNA (±S.E.M.) derived from K562 (Ph+ cell line), normal bone marrow (n=5), versus pre-imatinib (n=14), post-imatinib (n=4) and imatinib resistant (n=6) CML hematopoietic stem cells, common myeloid progenitors, granulocyte/macrophage progenitors or megakaryocyte/erythroid progenitors.

FIG. 4. A) Phase contrast photomicrograph (40×) of untransduced accelerated phase CML colonies, colonies derived from β-catenin-IRES-GFP transduced cells (center) and colonies derived from axin-IRES-GFP transduced cells (right). B) Graph of % replating efficiency of normal hematopoietic stem cells and granulocyte/macrophage progenitors with or without lentivirally enforced expression of axin and β-catenin. C) The % replating efficiency of normal versus CML (n=3) hematopoietic stem cells and granulocyte/macrophage progenitors before and after transduction with a lentiviral axin-GFP vector.

FIG. 8. LEF/TCF-GFP reporter assay of activated β-catenin in colonies derived from normal (left) or blast crisis CML (right) CD34$^+$Lin$^-$ cells.

FIG. 14. Analysis of engraftment of Imatimib resistant CML lentiviral luciferase transduced cells in immunodeficient mice.

DETAILED DESCRIPTION OF THE EMBODIMENTS

Figure 2:
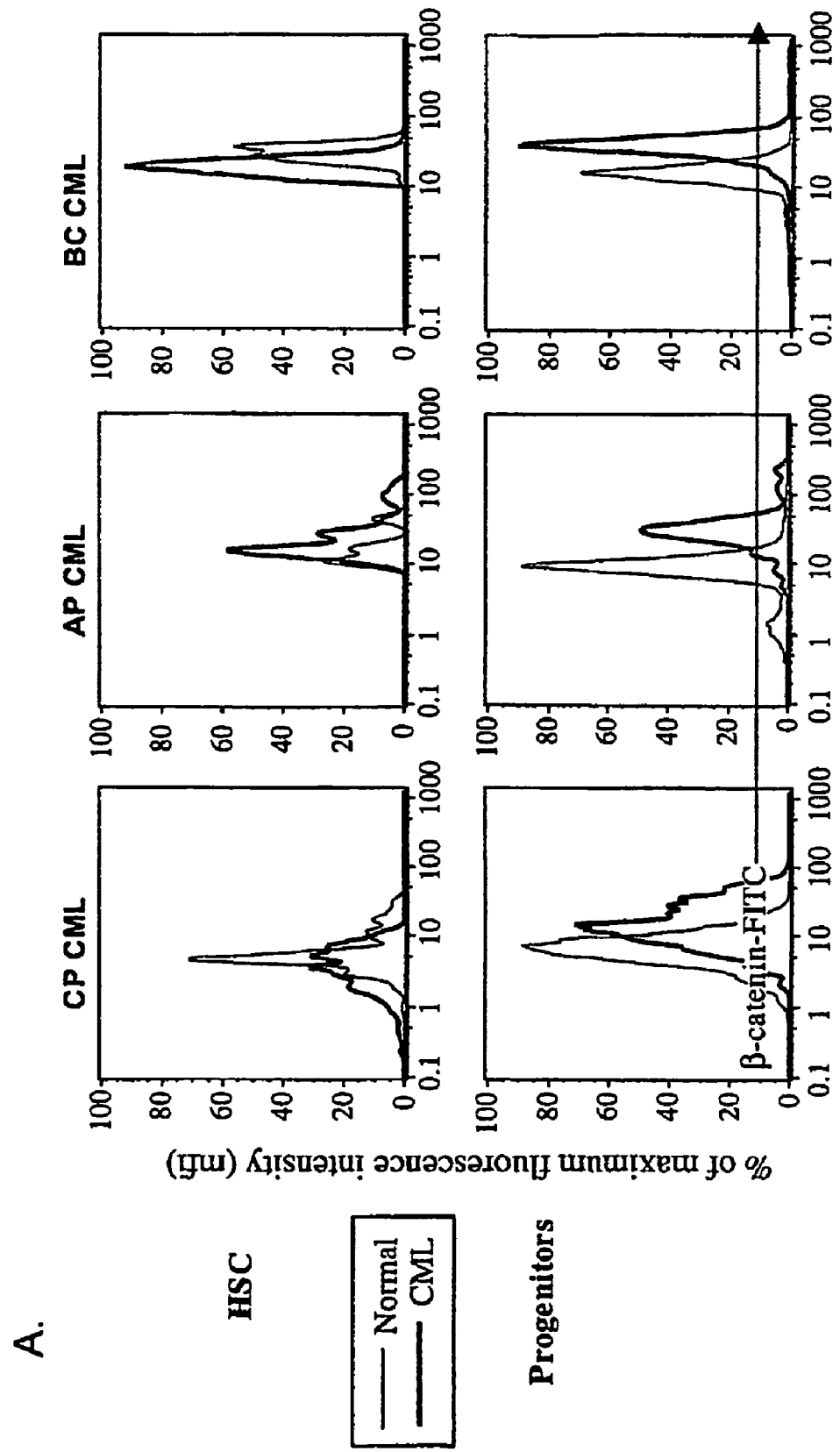
FIG. 2. A) Mean fluorescence intensity (MFI) of β-catenin-FITC in hematopoietic stem cells from normal versus chronic phase (Student's two-tailed unpaired T-test p=0.36), accelerated phase (P=0.30) and blast crisis (P=0.33) CML (upper panel), and in myeloid progenitors from normal versus chronic phase (P=0.963), accelerated phase (P=0.009) and blast crisis (P=0.04) CML (lower panel). Histograms are representative of β-catenin levels in 6 normal, 5 chronic phase, 5 accelerated phase and 4 blast crisis samples. B) Representative MFI of β-catenin-FITC in normal (n=6) vs. pre-imatinib blast crisis (n=3) hematopoietic stem cells (left), normal vs. pre-imatinib blast crisis CML progenitors (center), and normal vs. post-imatinib progenitors (right). Hematopoietic stem cells are $CD34^+CD38^-CD90^+Lin^-$ progenitors are $CD34^+CD38^+IL3R\alpha^+Lin^-$. There was a statistically significant difference in β-catenin MFI between CML accelerated phase (P=0.025) and blast crisis (P=0.027) progenitors pre and post-imatinib.
Figure 2:
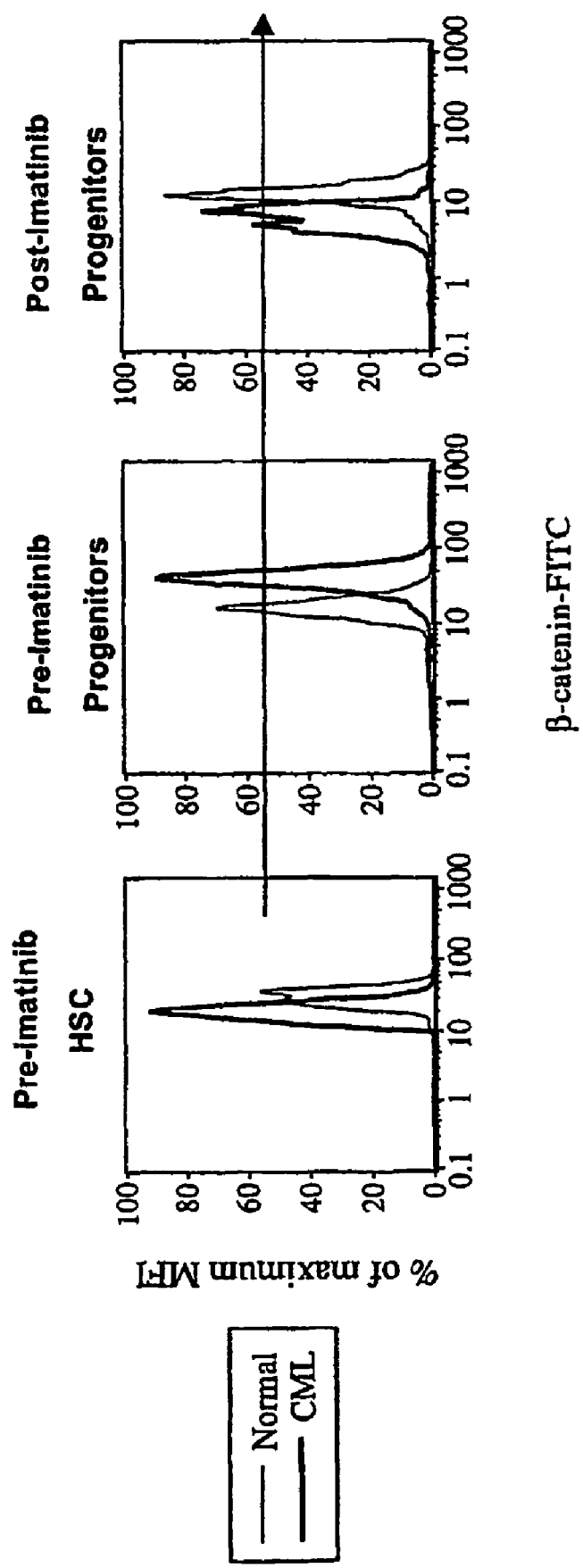

Leukemias and pre-leukemias, particularly chronic leukemias, e.g. chronic myelogenous leukemia (CML); chronic myelomonocytic leukemia, etc. are staged by analysis of the presence of hematopoietic stem and/or progenitor cells, particularly progenitor cells dedicated to the myeloid lineage, which progenitor cells may include CMP (common myeloid progenitors); megakaryocyte erythroid progenitors (MEP), and myelomonocytic lineages (GMP). Staging is useful for prognosis and treatment.

In one embodiment of the invention, a blood sample from a leukemia patient is stained with reagents specific for CD34; CD38; optionally a lineage panel; and one or more markers of CD90 (thy-1); flk-2; IL-3Rα; CD45RA; IL-7R. The analysis of staining patterns in the CD34+ subset of blood cells provides the relative distribution of progenitor cells, which distribution predicts the stage of leukemia.

In one embodiment of the invention, a leukemia patient sample is stained with a cocktail of reagents comprising binding partners specific for CD34, CD38, IL-3α, and CD45RA, where the distribution of hematopoietic stem cells (CD34$^+$CD38$^-$); common myeloid progenitor cells (CD34$^+$CD38$^+$CD45RA$^-$ IL-3Rα$^{lo}$); or myelomonocytic lineages progenitors (CD34$^+$CD38$^+$ CD45RA$^+$IL-3Rα$^{lo}$), and erythroid/megakaryocytic lineage progenitor (CD34$^+$CD38$^+$CD45RA$^{31}$IL-3Rα$^-$) distinguishes the progression of CML in the patient. Such methods include determination of activated β-catenin levels in a patient sample, e.g. a blood sample; enumeration of the granulocyte/macrophage progenitors present in a patient sample, and the like.

In one embodiment, the patient sample is compared to a control, or a standard test value. In another embodiment, the patient sample is compared to a pre-leukemic sample, or to one or more time points through the course of the disease.

Samples containing white blood cells, particularly including blood samples, are stained with reagents specific for markers present of hematopoietic stem and progenitor cells, which markers are sufficient to distinguish the major stem and progenitor groups. The reagents, e.g. antibodies, may be detectably labeled, or may be indirectly labeled in the staining procedure. The data provided herein demonstrate that the number and distribution of progenitor cells is diagnostic of the stage of the leukemia.

Any combination of markers may be used that are sufficient to distinguish the stem/progenitor cells of interest. A marker combination of interest may include CD34 and CD38, which distinguishes hematopoietic stem cells, (CD34$^+$, CD38$^-$) from progenitor cells, which are CD34$^+$, CD38$^+$). The inclusion of CD45RA and IL-3Rα is also of interest because it allows a distinction between the three known myeloid progenitor cell subsets. In other embodiments, CD90 may be included. CD47 and Flk2 are found to be indicative of CMML. Lineage panels may be included to distinguish progenitor cells from lineage committed cells.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

In another embodiment of the invention, lentiviral vectors expressing a fluorescent protein, e.g. green fluorescent protein (GFP) and variants thereof, including luciferase-GFP, are introduced into a cell or population of cells, where the construct comprises sequences encoding a detectable marker. The marker is optionally operably linked to a transcriptional response element regulated by β-catenin. In the presence of active, nuclear β-catenin, the detectable marker is expressed. Viable cells expressing GFP can be sorted, in order to isolate or enrich for the stem cells of interest. In this aspect, the methods may be used to track the engraftment and/or leukemic potential of a cell of interest. Of particular interest is the ability to trace the position and number of transduced cells in vivo, which can be followed over time without sacrificing the host animal.

Characterization of Leukemia Stem Cells

Leukemia stem cells may be responsible for progression and drug resistance in leukemias. The LSC provided herein are shown to have the phenotype similar to that of a hematopoietic progenitor cell, but altered in that the cells have acquired the proliferative and self-renewal capacity that is normally restricted to hematopoietic stem cells.

With respect to myelogenous leukemias, e.g. CML, AML, etc., the phenotype of myeloid lineage progenitors is useful in identification of LSC. These progenitor cells stain negatively for the markers Thy-1 (CD90), IL-7Rα (CD127); and with a panel of lineage markers, which lineage markers may include CD2; CD3; CD4; CD7; CD8; CD10; CD11b; CD14; CD19; CD20; CD56; and glycophorin A (GPA) in humans and CD2; CD3; CD4; CD8; CD19; IgM; Ter110; Gr-1 in mice. With the exception of the mouse MEP subset, all of the progenitor cells are CD34 positive. In the mouse all of the progenitor subsets may be further characterized as Sca-1 negative, (Ly-6E and Ly-6A), and c-kit high. In the human, all three of the subsets are $CD38^+$.

In the presence of steel factor (SLF), flt-3 ligand (FL), interleukin (IL)-3, IL-11, GM-CSF, thrombopoietin (Tpo) and erythropoietin (Epo), the CMP cells give rise to various types of myeloerythroid colonies, including CFU-GEMMeg, burst-forming unit-erythroid (BFU-E), CFU-megakaryocytes (CFU-Meg), CFU-granulocyte/macrophage (CFU-GM), CFU-granulocyte (CFU-G) and CFU-macrophage (CFU-M). The GMP subset generates CFU-M, CFU-G, or CFU-GM colonies containing macrophages and/or granulocytes in response to the above growth factors. In contrast, the MEP subset gives rise to CFU-Meg, BFU-E, or CFU-MEP colonies containing only megakaryocytes and/or erythrocytes in response to IL-3, GM-CSF, Tpo and Epo, but do not form colonies in the absence of Tpo and Epo. All three myeloid progenitor populations do not require "early-acting cytokines" such as SLF, FL and IL-11 to initiate colony formation.

All of these progenitors are capable of rapid differentiation activity in vivo. CMP cells give rise to Gr-1+/Mac-1+ myelomonocytic cells and megakaryocytic colonies, as well as TER119+ erythroid cells in spleen and bone marrow. The GMP progenitor population gives rise to Gr-1+/Mac-1+ cells; and the MEP progenitor population to megakaryocytes and erythroid cells.

The LSC identified in CML (CML-LSC) are shown to have a phenotype similar to that of the GMP, in that they are CD34+CD38+IL-3Rα+CD45RA+ and negative for the panel of lineage markers, which may comprise CD2; CD3; CD4; CD7; CD8; CD10; CD11b; CD14; CD19; CD20; CD56; and glycophorin A (GPA). The cells are capable of self-renewal in vitro; and have an activated β-catenin pathway, which can be inhibited with axin.

Other progenitor subsets that may find use in characterization of LSC include the common lymphoid progenitor, e.g. in analysis of lymphocytic leukemias. Common lymphoid progenitors, CLP, express low levels of c-kit (CD117) on their cell surface. Antibodies that specifically bind c-kit in humans, mice, rats, etc. are known in the art. Alternatively, the c-kit ligand, steel factor (Slf) may be used to identify cells expressing c-kit. The CLP cells express high levels of the IL-7 receptor alpha chain (CDw127). Antibodies that bind to human or to mouse CDw127 are known in the art. Alternatively, the cells are identified by binding of the ligand to the receptor, IL-7.

Human CLPs express low levels of CD34. Antibodies specific for human CD34 are commercially available and well known in the art. See, for example, Chen et al. (1997) *Immunol Rev* 157:41-51. Human CLP cells are also characterized as CD38 positive and CD10 positive.

The CLP subset also has the phenotype of lacking expression of lineage specific markers, exemplified by B220, CD4, CD8, CD3, Gr-1 and Mac-1. The CLP cells are characterized as lacking expression of Thy-1 (CD90), a marker that is characteristic of hematopoietic stem cells. The phenotype of the CLP may be further characterized as Mel-14$^-$, CD43$^{lo}$, HSA$^{lo}$, CD45$^+$ and common cytokine receptor γ chain positive.

The analysis of megakaryocyte progenitors may also be of interest, for example with respect to megakaryocytic forms of AML. The MKP cells are positive for CD34 expression, and tetraspanin CD9 antigen. The CD9 antigen is a 227-amino acid molecule with 4 hydrophobic domains and 1 N-glycosylation site. The antigen is widely expressed, but is not present on certain progenitor cells in the hematopoietic lineages. The MKP cells express CD41, also referred to as the glycoprotein IIb/IIIa integrin, which is the platelet receptor for fibrinogen and several other extracellular matrix molecules, for which antibodies are commercially available, for example from BD Biosciences, Pharmingen, San Diego, Calif., catalog number 340929, 555466. The MKP cells are positive for expression of CD117, which recognizes the receptor tyrosine kinase c-Kit. Antibodies are commercially available, for example from BD Biosciences, Pharmingen, San Diego, Calif., Cat. No. 340529. MKP cells are also lineage negative, and negative for expression of Thy-1 (CD90).

Leukemias

Chronic leukemias include chronic myelogenous leukemia (CML); chronic myelomonocytic leukemia, and chronic lymphocytic leukemia. Clonal myeloproliferation of CML is caused by malignant transformation of an early hematopoietic cell, and is characterized clinically by striking overproduction of granulocytes, primarily in the bone marrow but also in extramedullary sites. The neoplastic clone may include RBC, megakaryocyte, monocyte, and even some T and B cells. Normal stem cells are retained and can emerge after drug suppression of the CML clone. In most patients, the CML clone progresses to an accelerated phase and final blast crisis.

In the symptomatic patient, the WBC count is usually elevated and left shifted. The platelet count is normal or moderately increased. On blood smears, all stages of granulocyte differentiation are seen. The absolute eosinophil and basophil concentrations can be strikingly increased, but the absolute lymphocyte and monocyte concentrations may be normal. The bone marrow is hypercellular on aspirate and biopsy. The Philadelphia chromosome can be demonstrated in almost all patients by chromosomal analysis.

During the accelerated phase of disease progression, anemia and thrombocytopenia develop, basophils may increase, granulocyte maturation may be defective and the proportion of immature cells may increase. Further evolution may lead to a blast crisis with myeloblasts, lymphoblasts, or megakaryoblasts.

Imatinib mesylate is the drug of choice for most cases, although patients may also be treated with interferon, hydroxyurea, cytarabine, and other myelosuppressive drugs such as 6-mercaptopurine, 6-thioguanine, melephalan, and cyclophosphamide. In the absence of hematopoietic progenitor cell transplantation, for most cases the Ph-positive clone persists in the marrow.

Chronic Myelomonocytic Leukemias (CMML) include two types: an adult type referred to as CMML and a form of childhood leukemia called Juvenile Myelomonocytic Leukemia (JMML) or Juvenile Chronic Myelogenous Leukemia (JCML). CMML leukemias have features that are characteristic of myelogenous leukemia. CMML is more rapidly progressive than "typical" chronic myelogenous leukemia and less rapidly progressive than acute myelomonocytic leukemia.

JMML occurs most often in infants and children under four years of age. The blood cell and bone marrow findings are similar in some respects to adult chronic myelomonocytic leukemia. Both disorders are cancers that originate in a marrow cell. Infants with JMML fail to thrive. Low hemoglobin (anemia), low platelets, and moderate increases in white cell count are common. The blood invariably has an increased concentration of monocytes and immature granulocytes (myelocytes), hence the term "myelomonocytic" leukemia. The Ph chromosome, characteristic of typical chronic myelogenous leukemia is not present. JMML has been resistant to chemotherapy. The median survival of patients with the juvenile form of the disease is usually less than two years.

Adult type chronic myelomonocytic leukemia is part of the spectrum of myeloproliferative diseases that may have findings that simulate typical chronic myelogenous leukemia (CML) such as anemia, high white cell count and enlargement of the spleen except that there is an increase in monocytes rather than granulocytes. The cells do not contain the Ph chromosome, or BCR-ABL oncogene, that characterizes chronic myelogenous leukemia. Most patients with chronic myelomonocytic leukemia (CMML) are over 50 years of age. Blood cell counts may be variable with CMML. The white blood cell count may be slightly decreased, normal, or moderately elevated. There are two forms of CMML—a dysplastic form, MDS-CMML, with less than $13 \times 10^9/L$ monocytes versus a proliferative form, MPD-CMML, with $>13 \times 10^9/L$ monocytes. Blood myeloblasts may be absent or, when present, are in low proportions. In some cases, a translocation of chromosomes 5 and 12, occurs, resulting in the PDGFR-β-TEL gene translocation.

Chronic leukocytic leukemia (CLL) is the clonal expansion of mature-appearing lymphocytes involving bone marrow, lymph nodes and other lymphoid tissues with progressive infiltration of the liver and spleen. Most cases are diagnosed in elderly patients. Lymphocyte accumulation probably begins in the bone marrow and spreads to lymph nodes and other lymphoid tissues. Usually in late disease, abnormal hematopoiesis results in anemia, neutropenia, thrombocytopenia, and decreased immunoglobulin production. Traditional delineation of CLL has been of the most common subtype (B-cell form), which represents almost all cases, and a rare T cell type. In addition, other chronic leukemic patterns have been categorized under CLL: prolymphocytic leukemia, leukemic phase of cutaneous T-cell lymphoma, hairy cell leukemia, and lymphoma leukemia.

The hallmark of CLL is sustained, absolute lymphocytosis and increased lymphocytes in the bone marrow. CBC and bone marrow aspiration confirm diagnosis. Although CLL is progressive, some patients may be asymptomatic for years; therapy is not indicated until active progression or symptoms occur. Specific therapy includes chemotherapy, corticosteroids, and radiotherapy. Alkylating drugs, especially chlorambucil, alone or with corticosteroids, fludarabine, cyclophosphamide, pentostatin, rituximab and campath are also of use.

Acute leukemias are rapidly progressing leukemia characterized by replacement of normal bone marrow by blast cells of a clone arising from malignant transformation of a hematopoietic stem or progenitor cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas).

The presenting symptoms include fatigue, bleeding and infections and reflect the failure of normal hematopoiesis. Anemia and thrombocytopenia are very common (75 to 90%). The WBC count may be decreased, normal, or increased. Blast cells are usually found in the blood smear unless the WBC count is markedly decreased. The blasts of ALL can be distinguished from those of AML by histochemical studies, cytogenetics, immunophenotyping, and molecular biology studies. In addition to smears with the usual stains, terminal transferase, myeloperoxidase, Sudan black B, and specific and nonspecific esterase.

ALL is the most common malignancy in children, with a peak incidence from ages 3 to 5 yr. It also occurs in adolescents and has a second, lower peak in adults. Typical treatment emphasizes early introduction of an intensive multidrug regimen, which may include prednisone, vincristine, anthracycline or asparaginase. Other drugs and combinations are cytarabine and etoposide, and cyclophosphamide. Relapse usually occurs in the bone marrow but may also occur in the CNS or testes, alone or concurrent with bone marrow. Although second remissions can be induced in many children, subsequent remissions tend to be brief.

The incidence of AML increases with age; it is the more common acute leukemia in adults. AML may be associated with chemotherapy or irradiation (secondary AML). Remission induction rates are lower than with ALL, and long-term disease-free survival reportedly occurs in only 20 to 40% of patients. Treatment differs most from ALL in that AML responds to fewer drugs. The basic induction regimen includes cytarabine; along with daunorubicin or idarubicin. Some regimens include 6-thioguanine, etoposide, vincristine, and prednisone.

Pre-Leukemic Conditions

Myelodysplastic syndrome (MDS) represents a spectrum of defective hematopoiesis (see WHO classification) commonly seen in older patients. Exposure to carcinogens may by implicated. MDS is characterized by abnormal maturation of hematopoietic cells, including erythroid, myeloid, and megakaryocytic forms. The bone marrow is normal or hypercellular, and ineffective hematopoiesis causes variable cytopenias, the most frequent being anemia. The disordered cell production is also associated with morphologic cellular abnormalities in marrow and blood. Occasionally, extramedullary hematopoiesis may occur, leading to hepatomegaly and splenomegaly. Myelofibrosis is occasionally present at diagnosis or may develop during the course of MDS. The MDS clone is unstable and tends to progress to AML.

Anemia is the most common clinical feature, associated usually with macrocytosis and anisocytosis. Some degree of thrombocytopenia is usual; on blood smear, the platelets vary in size, and some appear hypogranular. The WBC count may be normal, increased, or decreased. Neutrophil cytoplasmic granularity is abnormal, with anisocytosis and variable numbers of granules. Eosinophils also may have abnormal granularity. A monocytosis is characteristic of the chronic myelomonocytic leukemia subgroup, and immature myeloid cells may occur in the less well differentiated subgroups. The prognosis is highly dependent on classification and on any associated disease. Response of MDS to AML chemotherapy is similar to that of AML, after age and karyotype are considered.

Differential Cell Analysis

The presence of LSC in a patient sample can be indicative of the stage of the leukemia. In addition, detection of LSC can be used to monitor response to therapy and to aid in prognosis. The presence of LSC can be determined by quantitating the cells having the phenotype of the progenitor cell relevant to the specific leukemia. For example, in CML it is useful to quantitate the number of cells having a GMP phenotype.

In addition to cell surface phenotyping, it is useful to quantitate the cells in a sample that have a "stem cell" character. This can be determined by determining the ability of the cells to self-renew and proliferate in culture; or by determining the presence of activated β-catenin pathway in these cells. For example, a nucleic acid construct may be introduced into a cell or population of cells, where the construct comprises sequences encoding a detectable marker, which marker is operably linked to a transcriptional response element regulated by β-catenin. In the presence of active, nuclear β-catenin, the detectable marker is expressed, and indicates that a cell is a stem cell. In some embodiments of the invention, the detectable marker is a fluorescent protein, e.g. green fluorescent protein (GFP) and variants thereof. Viable cells expressing GFP can be sorted, in order to isolate or enrich for the stem cells of interest. In this aspect, the methods may be used to enrich for LSC.

In addition to the presence of LSC, analysis of normal and leukemic hematopoietic samples allows determination of the stage of a leukemia. During progression of leukemic disease, which as used herein may refer to pre-leukemic and leukemic conditions, there is a significant expansion of $CD34^+$ cells in the blood, and a dramatic decline in these populations after successful drug treatment. Even more striking is the identification herein of shifting distributions of cells within this compartment, where the differential distribution of cells in the HSC, CMP, MEP and GMP populations is highly correlated with the stage of disease in myelogenous leukemias. The distribution of cells in lymphocytic leukemias may also be diagnostic, particularly the distribution between HSC and lymphoid committed progenitors.

For patients with adult CMML, the hematopoietic stem cells in blood increase relative to normal samples. The HSC compartment is also increased in drug resistant CML, relative to both normal and other stages of the disease. CML accelerated phase is also distinguished from chronic or blast crisis phase CML by consistently aberrant expression of CD90 by CD34+CD38+ cells. CML blast crisis is typified by an expansion of both $CD34^+CD38^-$ and $CD34^+CD38^+$ progenitors.

Cell surface expression of Flk2/Flt3, a tyrosine kinase that is frequently mutated or overexpressed in poor prognosis AML, is elevated in $CD34^+CD38^-CD90^+$ and $CD90^-Lin^-$ cells in advanced phases of CML.

Differential analysis of committed myeloid progenitor profiles ($CD34^+CD38^+Lin^-$) provides a means of distinguishing chronic, accelerated and blast crisis. Chronic phase is typified by an expansion of megakaryocyte erythroid progenitors (MEP). Accelerated phase is characterized by increased common myeloid progenitors (CMP). Myeloid blast crisis is characterized by a greater proportion of granulocyte macrophage progenitors (GMP) compared with normal bone marrow In imatinib responsive patients the proportion of individual myeloid progenitors reverted to normal, whereas imatinib resistant bone marrow or peripheral blood demonstrated an expansion of both HSCs and GMPs more typical of blast crisis.

Clinical samples for use in the methods of the invention may be obtained from a variety of sources, particularly blood, although in some instances samples such as bone marrow, lymph, cerebrospinal fluid, synovial fluid, and the like may be used. Such samples can be separated by centrifugation, elutriation, density gradient separation, apheresis, affinity selection, panning, FACS, centrifugation with Hypaque, etc. prior to analysis, and usually a mononuclear fraction (PBMC) will be used. Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

The labeled cells are quantitated as to the expression of cell surface markers. It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a conjugate of an enzyme with progenitor cell specific antibodies.

The comparison of a differential progenitor analysis obtained from a patient sample, and a reference differential progenitor analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Cell Surface Staining Methods

Analysis by cell staining may use conventional methods, as known in the art. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers as previously described. It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a conjugate of an enzyme with progenitor cell specific antibodies.

Analysis of β-Catenin Activation

A mixed population of cells, or a population enriched for LSC may be analyzed for activation of the β-catenin pathway. A nucleic acid construct is introduced into a cell or population of cells, where the construct comprises sequences encoding a detectable marker, which marker is operably linked to a transcriptional response element regulated by β-catenin, herein termed a "detection construct". In the presence of nuclear β-catenin, the detectable marker is expressed, and indicates that a cell is a stem cell. In this aspect, the method may be used to determine whether a test cell is a stem cell. Viable cells expressing the marker can also be sorted, in order to isolate or enrich for the stem cells of interest.

A variety of vectors are known in the art for the delivery of sequences into a cell, including plasmid vectors, viral vectors, and the like. In a preferred embodiment, the vector is a retroviral or lentiviral vector. For example, see Baum et al. (1996) J Hematother 5(4):323-9; Schwarzenberger et al. (1996) Blood 87:472-478; Nolta et al. (1996) P.N.A.S. 93:2414-2419; and Maze et al. (1996) P.N.A.S. 93:206-210, Mochizuki et al. (1998) J Virol 72(11):8873-83. The use of adenovirus based vectors with hematopoietic cells has also been published, see Ogniben and Haas (1998) *Recent Results Cancer Res* 144:86-92.

The beta-catenin transcriptional response element (TRE) will comprise one or more nucleotide motifs that bind a transcription factor activated by β-catenin. In a preferred embodiment, the transcription factor is LEF/TCF (for a review, see Roose and Clevers (1999) Biochim Biophys Acta 1424(2-3):M23-37, herein incorporated by reference). Transcriptionally inert LEF/Tcf factors become potent transactivators upon interaction with beta-catenin in the nucleus. It may be noted that β-catenin is found in the cytoplasm, but its primary biological effects are seen when it is activated and translocated into the nucleus. Nucleotide elements responsive to this signaling pathway include, for example TBE1 (SEQ ID NO:1; CCTTTGATT) and TBE2 (SEQ ID NO:2; GCTTTGATC), which are contained on the human C-MYC promoter Kpnl to Pvull fragment, see He et al. (1998) *Science* 281:1509; LEF/TCF binding motifs, (e.g. SEQ ID NO:3; CCTTTGATC; or SEQ ID NO:4; CCTTTGGCC) (Korinek et al. (1997) *Science* 275:1784-1787); LEF-1 binding sites, SEQ ID NO:5; GCTTTGATCTT (Shtutman et al. (1999) *Proc Natl Acad Sci U S A* 96(10):5522-7), and otherwise as known in the art. There references are herein specifically incorporated by reference for their teaching of sequences responsive to LEF-1/TCF. The complement of these sequences may also be used, e.g. (SEQ ID NO:13) GATCAAAGGG.

In one embodiment of the invention, the β-catenin responsive TRE comprises one or more, two or more, three or more, etc. of a binding motif sequence (SEQ ID NO:12) $X^1$ C T T T G Pu T Py; where $X^1$ is G or C, Pu is purine and Py is pyrimidine. In a preferred embodiment the β-catenin responsive TRE comprises one or more, two or more, three or more, etc. of a binding motif sequence that is the complement of SEQ ID NO:12; (SEQ ID NO:14) 5' Pu A Py C A A A G $X^1$ 3', where $X^1$ is G or C, Pu is purine and Py is pyrimidine.

Operably linked to the β-catenin TRE is a detectable marker. Many such markers are known in the art, for example antibiotic resistance, color change of a substrate, expression of a recombinase, e.g. cre recombinase, FLP recombinase, pSR1 recombinase, etc., which is indirectly detected; expression of luminescence producing proteins, e.g. luciferase, green fluorescent proteins, etc.

In a preferred embodiment of the invention, the marker is a luminescence producing protein, preferably GFP. The native gene encoding this protein has been cloned from the bioluminescent jellyfish *Aequorea victoria* (Morin, J. et al., J Cell Physiol (1972) 77:313-318). The availability of the gene has made it possible to use GFP as a marker for gene expression. GFP itself is a 283 amino acid protein with a molecular weight of 27 kD. It requires no additional proteins from its native source nor does it require substrates or cofactors available only in its native source in order to fluoresce. (Prasher, D. C. et al., Gene (1992) 111:229-233; Yang, F. et al., Nature Biotechnol (1996) 14:1252-1256; Cody, C. W. et al., Biochemistry (1993) 32:1212-1218.) Mutants of the GFP gene have been found useful to enhance expression and to modify excitation and fluorescence. GFP-S65T (wherein serine at 65 is replaced with threonine) may be used, which has a single excitation peak at 490 nm. (Heim, R. et al., Nature (1995)

373:663-664); U.S. Pat. No. 5,625,048. Other mutants have also been disclosed by Delagrade, S. et al., Biotechnology (1995) 13:151-154; Cormack, B. et al., Gene (1996) 173:33-38 and Cramer, A. et al. Nature Biotechnol (1996) 14:315-319. Additional mutants are also disclosed in U.S. Pat. No. 5,625,048. By suitable modification, the spectrum of light emitted by the GFP can be altered. Thus, although the term "GFP" is used in the present application, the proteins included within this definition are not necessarily green in appearance. Various forms of GFP exhibit colors other than green and these, too, are included within the definition of "GFP" and are useful in the methods and materials of the invention. In addition, it is noted that green fluorescent proteins falling within the definition of "GFP" herein have been isolated from other organisms, such as the sea pansy, *Renilla reriformis*. Any suitable and convenient form of the GFP gene can be used in the methods of the invention.

Various techniques known in the art may be used to transfect the target cells, e.g. electroporation, calcium precipitated DNA, fusion, transfection, lipofection and the like. The particular manner in which the DNA is introduced is not critical to the practice of the invention.

Combinations of retroviruses and an appropriate packaging line may be used, where the capsid proteins will be functional for infecting the target cells. Usually, the cells and virus will be incubated for at least about 24 hours in the culture medium. Commonly used retroviral vectors are "defective", i.e. unable to produce viral proteins required for productive infection. Replication of the vector requires growth in the packaging cell line.

The host cell specificity of the retrovirus is determined by the envelope protein, env (p 120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of the β-catenin gene after integration into a target cell genome. For some uses, however, it is desirable to have a regulatable promoter driving expression. Where such a promoter is included, the promoter function of the LTR will be inactivated. This is accomplished by a deletion of the U3 region in the 3' LTR, including the enhancer repeats and promoter, that is sufficient to inactivate the promoter function. After integration into a target cell genome, there is a rearrangement of the 5' and 3' LTR, resulting in a transcriptionally defective provirus, termed a "self-inactivating vector".

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types, e.g. IL-2 promoter in T cells, immunoglobulin promoter in B cells, etc.

For detecting or selecting LSC, the detection construct is introduced into a cell or population of cells, suspected of being or comprising stem cells. After introduction of the expression construct, the cells are maintained for a period of time sufficient to express the detectable marker, usually at least about 12 hours and not more than about 2 weeks, and may be from about 1 day to about 1 week.

The cells may be obtained from any mammalian species, e.g. equine, bovine, porcine, canine, feline, rodent, e.g. mice, rats, hamster, primate, etc., particularly human. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−180° C.) indefinitely. Populations of cells include putative stem cell clones, tumor samples, bone marrow samples, embryonic stem cells, organs, e.g. neural crest, gut, spleen, liver, umbilical cord blood, peripheral blood, mobilized peripheral blood, yolk sac, etc.

The expression of the detectable marker, where the marker is a fluorescent protein, can be monitored by flow cytometry, where lasers detect the quantitative levels of fluorophore. Flow cytometry, or FACS, can also be used to separate cell populations based on the intensity of fluorescence, as well as other parameters such as cell size and light scatter. Although the absolute level of staining may differ, the data can be normalized to a control.

Screening for expression of β-catenin may be also based on the functional or antigenic characteristics of the protein, including the nuclear localization of the protein. Various immunoassays designed to detect polymorphisms may be used in screening. Detection may utilize staining of cells or histological sections, performed in accordance with conventional methods, using antibodies or other specific binding members that specifically bind to β-catenin. The antibodies or other specific binding members of interest are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

LSC Compositions

The cells of interest may be separated from a complex mixture of cells by techniques that enrich for cells having the above described characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for LSC are achieved in this manner. The subject population may be at or about 50% or more of the cell composition, and preferably be at or about 75% or more of the cell composition, and may be 90% or more. The desired cells are identified by their surface phenotype, by the ability to self-renew, an essential property of stem cells. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for LSC may be used in a variety of screening assays and cultures, as described below.

The enriched LSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, Flk-2 ligand, IL-11, IL-3, GM-CSF, erythropoietin, thrombopoietin, etc In addition to, or instead of growth factors, the subject cells may be grown in a co-culture with fibroblasts, stromal or other feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213-235) or "Dexter" culture conditions (Dexter et al. [1977] *J Exp Med* 145:1612-1616); and heterogeneous thymic stromal cells (Small and Weissman [1996] *Scand J Immunol* 44:115-121).

The comparison of a differential progenitor analysis; or an LSC analysis obtained from a patient sample, and a reference analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Screening Assays

LSC are also useful for in vitro assays and screening to detect factors and chemotherapeutic agents that are active on cancer stem cells. Of particular interest are screening assays for agents that are active on human cells. A wide variety of assays may be used for this purpose, including immunoassays for protein binding; determination of cell growth, differentiation and functional activity; production of factors; and the like.

In one embodiment of the invention, the LSC are inhibited by agents that interfere with β-catenin activation or expression. For example it has been shown that axin and other wnt inhibitors inhibit proliferation of LSC. Methods may include screening assays directed at β-catenin, or members of the β-catenin signaling pathway. Compounds for screening include pharmacophores of axin; axin mimetics; polynucleotides encoding axin operably linked to a promoter active in LSC; and other inhibitors of β-catenin or the β-catenin activation pathway.

As used herein, wnt inhibitors include any agents that downregulate expression or activity of wnt. Agents of interest may interact directly with wnt, e.g. blocking antibodies, or may interact with wnt associated proteins, e.g. Wnt co-receptors LRP5/6 and the transmembrane protein Kremen. A number of wnt inhibitors have been described and are known in the art, including those described above.

Among the known wnt inhibitors are members of the Dickkopf (Dkk) gene family (see Krupnik et al. (1999) Gene 238(2):301-13). Members of the human Dkk gene family include Dkk-1, Dkk-2, Dkk-3, and Dkk4, and the Dkk-3 related protein Soggy (Sgy). hDkks 1-4 contain two distinct cysteine-rich domains in which the positions of 10 cysteine residues are highly conserved between family members. Exemplary sequences of human Dkk genes and proteins are publicly available, e.g. Genbank accession number NM_014419 (soggy-1); NM_014420 (DKK4); AF177394 (DKK-1); AF177395 (DKK-2); NM_015881 (DKK3); and NM_014421 (DKK2).

Inhibitors may also include derivatives, variants, and biologically active fragments of Dkk polypeptides. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino add residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

A "chimeric" Dkk polypeptide is a polypeptide comprising a polypeptide or portion (e.g., one or more domains) thereof fused or bonded to heterologous polypeptide. The chimeric Wnt polypeptide will generally share at least one biological property in common with a native sequence Wnt polypeptide. Examples of chimeric polypeptides include immunoadhesins, combine a portion of the Dkk polypeptide with an immunoglobulin sequence, and epitope tagged polypeptides, which comprise a Dkk polypeptide or portion thereof fused to a "tag polypeptide". The tag polypeptide has enough residues to provide an epitope against which an antibody can be made, yet is short enough such that it does not interfere with biological activity of the Dkk polypeptide. Suitable tag polypeptides generally have at least six amino acid residues and usually between about 6-60 amino acid residues.

Other inhibitors of wnt include Wise (Itasaki et al. (2003) Development 130(18):4295-30), which is a secreted protein. The Wise protein physically interacts with the Wnt co-receptor, lipoprotein receptor-related protein 6 (LRP6), and is able to compete with Wnt8 for binding to LRP6. Axin regulates Wnt signaling through down-regulation of beta-catenin (see Lyu et al. (2003) J Biol Chem. 278(15):13487-95).

A soluble form of the ligand binding domain (CRD) of Frizzled has also been shown to inhibit wnt. The Frizzled-CRD domain has been shown to inhibit the Wnt pathway by inhibiting the binding of Wnts to the frizzled receptor (Hsieh et al. (1999) *Proc Natl Acad Sci U S A* 96:3546-51; and Cadigan et al. (1998) *Cell* 93:767-77). Polypeptides of interest include FRP5, FRP8, and the like. Similarly, SFRPs represent secreted molecules which encode Frizzled-like CRDs and thus represent soluble Wnt antagonists by functioning as soluble receptors (Krypta et al, J Cell Sci 2003 July 1; 116(Pt 13):2627-34).

In screening assays for biologically active agents, antiproliferative drugs; etc. the LSC composition, usually a culture comprising LSC, is contacted with the agent of interest, and the effect of the agent assessed by monitoring output parameters, such as expression of markers, cell viability, and the like. The cells may be freshly isolated, cultured, genetically altered as described above to provide a marker for activation of β-catenin, and the like. The cells may be environmentally induced variants of clonal cultures: e.g. split into independent cultures and grown under distinct conditions, for example with or without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 μl to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells. (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

Kits may be provided, where the kit will comprise a staining reagents that are sufficient to differentially identify the LSC, and/or $CD34^+$ stem and progenitor subsets described herein. A marker combination of interest may include CD34 and CD38, CD45RA and IL-3Rα. In other embodiments, CD90 may be included. CD47 and Flk2 are found to be indicative of CMML. Lineage panels may be included to distinguish progenitor cells from lineage committed cells. The staining reagents are preferably antibodies, and may be detectably labeled. Kits may also include tubes, buffers, etc., and instructions for use.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Experimental

Example 1

Fluorescence activated cell sorting (FACS) was used to prospectively isolate highly purified hematopoietic stem cells (HSCs) and myeloid progenitors from chronic phase (CP; n=20), accelerated phase (AP; n=24) and blast crisis (BC; n=12) phase CML bone marrow and peripheral blood samples before, during (CP=22, AP=11, BC=2) and after patients developed resistance to Imatinib (AP=4, BC=1).

Methods

Bone Marrow and Peripheral Blood Samples. Fresh human bone marrow was obtained with informed consent from healthy volunteers (AllCells, Berkeley, Calif.) as well as from allogeneic bone marrow donors (Department of Bone Marrow Transplantation, Stanford School of Medicine, Stanford, Calif.). Cytokine (G-CSF) mobilized peripheral blood samples were also obtained following apheresis from allogeneic donors. Chronic (CP; n=20), accelerated (AP; n=24) and blast crisis (BC; n=12) phase bone marrow and peripheral blood samples were obtained with informed consent from newly diagnosed patients referred to Stanford University Medical Center as well as from patients who had received imatinib for 6 to 16 months (CP=22, AP=11, BC=2) and those who became resistant to imatinib (AP=4, BC=1) who were enrolled on the farnesyl transferase inhibitor/imatinib study for imatinib refractory patients.

Hematopoietic Stem Cell and Myeloid Progenitor Flow Cytometric Analysis and Cell Sorting. Mononuclear fractions were extracted following Ficoll density centrifugation according to standard methods and analyzed fresh or subsequent to rapid thawing of samples previously frozen in 90% FCS and 10% DMSO in liquid nitrogen. Prior to FACS analysis and sorting, hematopoietic stem cells (HSCs) were stained with lineage marker specific phycoerythrin (PE)-Cy5-conjugated antibodies including CD2 RPA-2.10; CD11b, ICRF44;

CD20, 2H7; CD56, B159; GPA, GA-R2 (Becton Dickinson-PharMingen, San Diego), CD3, S4.1; CD4, S3.5; CD7, CD7-6B7; CD8, 3B5; CD10, 5-1B4, CD14, TUK4; CD19, SJ25-C1 (Caltag, South San Francisco, Calif.) and APC-conjugated anti-CD34, 84G12 (Becton Dickinson-Pharmingen), biotinylated anti-CD38, HIT2 (Caltag), FITC-conjugated anti-CD90 and PE conjugated anti-Flk2. Streptavidin-conjugated Texas red (GIBCO) was used to visualize biotinylated antibodies. HSCs were identified based on $CD34^+CD38^-CD90^+$ lineage negative (lin−) staining.

Myeloid progenitors were stained with the same lineage marker specific PE-Cy5-conjugated antibodies, APC-conjugated anti-CD34, 8G12 (Becton Dickinson-PharMingen) and biotinylated anti-CD38, HIT2 (Caltag) in addition to PE-conjugated anti-IL-3Rα, 9F5 (Becton Dickinson-ParMingen) and FITC-conjugated anti-CD45RA, MEM56 (Caltag) followed by staining with Streptavidin-Texas Red to visualize CD38-BIO stained cells and resuspension in propidium iodide to exclude dead cells. Unstained samples and isotype controls were included to assess background fluorescence. After staining, cells were analyzed and sorted using a modified FACS Vantage (Becton Dickinson Immunocytometry Systems, Mountain View, Calif.) equipped with a 599 nm dye laser and a 488 nm argon laser. Cells were double sorted or were clone sorted using an automatic cell-deposition unit (ACDU) system (Becton Dickinson). Hematopoietic stem cells (HSCs) were identified as $CD34^+CD38^-CD90^+$ lin−. Common myeloid progenitors (CMPs) were identified based on $CD34^+CD38^+IL-3R\alpha^+CD45RA^-$ lin− staining and their progeny including granulocyte/macrophage progenitors (GMPs) were $CD34^+CD38^+IL-3R\alpha^+CD45RA^+$ lin− while megakaryocyte/erythrocyte progenitors (MEPs) were identified based on $CD34^+ CD38^+IL-3R\alpha^-CD45RA^-$ lin− staining.

Hematopoietic Progenitor Assays. Myeloid colony formation by normal versus CML bone marrow and peripheral blood samples was assessed 14 days after sorting approximately 100 cells directly onto 35 mm petri dishes (Falcon) containing methylcellulose medium (Methocult, Stem Cell Technologies, Vancouver) supplemented with BSA, glutamine, 2-mercaptoethanol, antibiotics and human cytokines (R&D Systems) including IL-3 (20 ng/ml), IL-6 (10 ng/ml), IL-11 (10 ng/ml), stem cell factor (SCF, 10 ng/ml), Flt3 ligand (FL, 10 ng/ml), granulocyte/macrophage colony stimulating factor (GM-CSF, 50 ng/ml), thrombopoietin (TPO, 50 ng/ml) and erythropoietin (Epo, 4 Units/ml) and incubating them at 37° C. in a 7% $CO_2$ incubator. In serial replating experiments, individual colonies (4 to 17/plate) were plucked and replated in 200 µl of methylcellulose medium supplemented with IL-3, IL-6, IL-11, SCF, Flt3 ligand, GM-CSF, TPO and EPO and colonies were scored at 14 days as described above.

Confocal Fluorescence Microscopy. Cytospins of double FACS sorted progenitor populations derived from normal (n=5) bone marrow or CML (CP=2, AP=3, BC=4, post-imatinib=2, imatinib resistant=2) bone marrow or peripheral blood samples were prepared with a Shandon Cytospin Centrifuge (500 rpm) or alternatively, progenitor populations were sorted directly onto glass slides. Slides were washed for 5 min in PBS at RT, incubated for 1 hr with 1:50 anti-human CD45-FITC antibody (Anti-Hle-1; Becton Dickinson) in PBS at RT in a humid dark chamber followed by washing for 5 min with PBC in the dark. Slides were then fixed for 10 min with 4% paraformaldehyde and then washed for 5 min in PBS and 0.1% Tween-20 at RT in the dark. Non-specific antibody binding was blocked by adding 5% Goat serum, 1% BSA, 1:100 Fcγ Receptor in 0.1% Tween-20 and PBS for 1 hr at RT then slides were incubated for 1 hr at RT in humid dark chamber with 2.5 µg/ml of an antibody to non-phosphorylated-β-catenin (Clone 8E4 mouse monoclonal IgG; Upstate) diluted in 2% Goat serum and 1% BSA in PBS. Slides were then washed twice for 15 min with PBS and 0.1% Tween-20 at RT in the dark followed by a 1 hour incubation with an Alexa 594 conjugated goat anti-mouse antibody at a dilution of 1:1000 (Molecular Probes) in antibody dilution buffer. Cells were then washed twice for 15 min with PBS and 0.1% Tween-20, incubated for 10 min with a 1:1000 dilution in PBS of Hoechst 33342 (Molecular Probes) in PBS, washed for 5 min with PBS and 0.1% Tween-20 and then a cover slip was added with Prolong antifade (Molecular Probes).

Cells were stained with antibody specific for non-phosphorylated (activated) β-catenin (Jackson labs), followed by staining with Alexa 594 conjugated goat anti-mouse antibody and Hoechst 33342 as a nuclear stain as well as a FITC conjugated antibody to human CD45 to delineate the cell surface. Controls included isotype controls and secondary antibody only. Confocal images were obtained in multitrack mode with a dual photon Zeiss LSM 510 confocal fluorescence microscope. Excitation and emission spectra were 543 nm (100% transmission) and 565-615 nm, respectively for β-catenin-Alexa 594. To visualize Hoechst 33342, a dual photon laser system with a 776 nm excitation wavelength and with a beam splitter and band pass of 435-485 nm (20.9% transmission) was employed while the excitation wavelength for to visualize CD45 FITC was 488 nm at 10.9% transmission. Three dimensional renderings of confocal images were made with Volocity™ software.

LEF/TCF Reporter Assay. A lentiviral LEF/TCF reporter was made in which the enhanced GFP (eGFP) gene was cloned downstream of a LEF-1/TCF-responsive promoter, containing three LEF-1/TCF binding motifs and a TATA box. This cassette was then cloned into a self-inactivating lentiviral transfer vector plasmid. The virus was produced by co-transfection of the transfer vector with the VSVG envelope-encoding plasmid pMD.G, and the packaging plasmid CMVΔR8.74 into 293T cells. The supernatant was harvested and concentrated by ultracentrifugation. LEF/TCF-IRES-GFP vector (1/100) or no vector were added at a dilution of 1:100 directly into 200 microliter wells containing hematopoietic stem and progenitor populations that were clone sorted (200-1000 cells/well) directly into 96 well plates containing 150 µl of Iscoves Modified Dulbecco's media (IMDM) supplemented with 10% fetal bovine serum, glutamine, antibiotics (Pen-Strep) and cytokines including IL-6 (10 ng/ml), Flt3 ligand (50 ng/ml), stem cell factor (SCF; 50 ng/ml) and thrombopoietin (TPO; 10 ng/ml). Cells were incubated in a 37° C., 7% $CO_2$ incubator for 7 days and then harvested, washed, resuspended in propidium iodide and analyzed for GFP expression using FACS analysis (FACS Vantage). Normal and CML mononuclear cells, HSC and GMP were transduced with the LEF/TCF-IRES-GFP (1:100) or no vector in methylcellulose medium (Stem Cell Technologies, Vancouver) supplemented with IL-3, IL-4, IL-11, Flt3 ligand, GM-CSF, SCF, TPO and EPO and cultured for 14 days in a 37° C. 7% $CO_2$ incubator as described above. GFP expression in colonies was visualized using a Zeiss inverted microscope and photographed with the aid of SPOT software. Non-transduced colonies were used as autofluorescence controls.

Results

Five color FACS analysis of normal and hematopoietic stem cell profiles revealed an expansion of CD34+lin− cells in CML bone marrow and peripheral blood samples prior to Imatinib but a dramatic decline in CD34+Lin− progenitors post-imatinib therapy. Disease progression to accelerated phase was marked by an expansion of the CD34+CD38+Lin− progenitor pool (P=0.026) compared with normal bone marrow. While the HSC compartment did not expand significantly in CML CP and AP, it did increase in imatinib resistant CML samples. CML AP could also be distinguished from chronic or blast crisis phase CML by consistently aberrant expression of CD90 by CD34+CD38+ cells. CML blast crisis was typified by an expansion of both CD34+CD38− (p=0.01) and CD34+CD38+ progenitors. Furthermore, cell surface expression of Flk2/Flt3, a tyrosine kinase that is frequently mutated or overexpressed in poor prognosis AML, was elevated in CD34+CD38−CD90+ and CD90−Lin− cells in advanced phases of CML.

Examination of committed myeloid progenitor profiles (CD34+CD38+Lin−) by FACS analysis using recently identified cell surface markers, demonstrated that chronic, accelerated and blast crisis had characteristic progenitor profiles. While CML CP was typified by an expansion of megakaryocyte erythroid progenitors (MEPs; p=0.0000369), CML AP was characterized by increased common myeloid progenitors (CMPs; p=0.004), and myeloid blast crisis samples had a greater proportion of granulocyte macrophage progenitors (GMPs; p=0.02) compared with normal bone marrow (FIG. 1Aiii and FIG. 1C and FIGS. 1C and D). In imatinib responsive patients, although the number of CD34+CD38− and CD34+CD38+ cells decreased, the proportion of individual myeloid progenitors reverted to normal whereas imatinib resistant bone marrow or peripheral blood demonstrated an expansion of both HSCs and GMPs more typical of BC phase CML. There is also an expansion of hematopoietic stem cells in post-imatimib CML.

In order to ascertain the role of BCR-ABL in CML HSC and myeloid progenitor expansion, we performed quantitative RT-PCR of BCR-ABL expression on highly purified HSC and myeloid progenitors derived from CML CP, AP and BC bone marrow and peripheral blood before and after imatinib therapy. While BCR-ABL in HSC did not change significantly with progression of disease from CML CP to BC, there was a marked increase in BCR-ABL expression by myeloid progenitors such as CMP and GMP. The levels of BCR-ABL decreased in both HSCs and myeloid progenitors in imatinib responsive patients but increased in HSCs and GMPs in imatinib resistant patients.

Five color FACS analysis of progenitor profiles, quantitative RT-PCR of BCR-ABL expression and FACS analysis of intracellular β-catenin levels revealed that CML progression was marked by an expansion of both HSCs and GMPs which overexpressed BCR-ABL and by an increase in β-catenin expression by myeloid progenitors. Similarly, confocal fluorescence microscopy using an antibody to activated (non-phosphorylated) β-catenin and a LEF/TCF reporter assay both demonstrated that myeloid progenitors rather than HSC had elevated levels of nuclear β-catenin. Imatinib resistant CML demonstrated expansion of the myeloid progenitor pool and coincident overexpression of β-catenin. Transduction of CML progenitors with β-catenin resulted in increased colony size while transduction with its inhibitor, axin, decreased colony size.

Example 2

Similar experiments were performed with blood samples from CMML patients. The data demonstrate an increase in Flk2 expression by hematopoietic stem cells in a CMML patient.

TABLE 1

|  | 90+ FLK2− % | 90+ FLK2+ % | 90− FLK2+ % | 90− FLK2− % |
|---|---|---|---|---|
| NBM (N = 4) | 39 | 23 | 9 | 26 |
| CMML (N = 4) | 11 | 12 | 48 | 28 |

There is an increase of common myeloid progenitors (CMP) in a CMML patient, and as shown in Table 2.

|  | MEP | CMP | GMP | IL-3R++ 45RA+ |
|---|---|---|---|---|
| NBM (n = 4) | 19 | 26 | 31 | 17 |
| CMML (n = 5) | 4 | 65 | 15 | 8 |

Example 3

The progression of chronic myelogenous leukemia (CML) to blast crisis, which is supported by self-renewing leukemic stem cells. Normal mouse hematopoietic stem cells use the Wnt/β-catenin signaling pathway for self-renewal. We investigated whether leukemic stem cells in CML use the β-catenin pathway for self-renewal.

Methods

Bone Marrow and Peripheral Blood Samples. Bone marrow (All Cells, Berkeley, Calif.; n=11) or G-CSF mobilized peripheral blood, were obtained from healthy volunteers as previously described, or from patients with CML in chronic phase (n=20), accelerated phase (n=26) or blast crisis (n=13) after obtaining written informed consent and according to Stanford University and UCLA IRB regulations. Cells were obtained from patients before treatment with imatinib, and from patients who had received imatinib for 6 to 15 months (chronic phase; n=22, accelerated phase; n=11, blast crisis; n=2) and imatinib-resistant patients (accelerated phase; n=5, blast crisis; n=1). Patients in chronic phase received interferon alpha while patients with advanced disease were often treated with cytoreductive agents in addition to imatinib (Table 1).

TABLE 1

| Pt. | Age | Sex | Type | Phase at Time of Sample Analysis | Prior Therapy |
|---|---|---|---|---|---|
| A) Characteristics of Pre-Imatinib CML Patient Samples ||||||
| 1 | 76 | M | BM | CP, 100% Ph+ | IFN-α |
| 2 | 27 | M | BM | CP, 100% Ph+ | IFN-α |
| 3 | 40 | F | BM | CP, 100% Ph+ | IFN-α/ara-C |

TABLE 1-continued

| Pt. | Age | Sex | Type | Phase at Time of Sample Analysis | Prior Therapy |
|---|---|---|---|---|---|
| 4 | 49 | M | BM | CP, 100% Ph+ | IFN-α/Hydrea |
| 5 | 46 | M | BM | AP, 81% Ph+/clonal evolution trisomy 8 | IFN-α |
| 6 | 66 | M | BM | AP, 100% Ph+/clonal evolution | IFN-α/ara-C/homoharringtonine + ara-C/Hydrea |
| 7 | 53 | M | BM | AP, 100% Ph+/clonal evolution trisomy 8 | IFN-α/Hydrea/6-MP |
| 8 | 71 | M | PB | AP, 100% Ph+ | IFN-α/Hydrea |
| 9 | 63 | F | BM | AP, 100% Ph+ | Hydrea + ATRA |
| 10 | 32 | M | PB | AP, 100% Ph+/clonal evolution | Hydrea |
| 11 | 41 | M | PB | AP | Hydrea |
| 12 | 62 | M | BM | Myeloid BC, 100% Ph+/clonal evolution | IFN-α/Hydrea |
| 13 | 81 | F | PB | Myeloid BC, 100% Ph+ | none |
| 14 | 67 | F | PB | Lymphoid BC, 100% Ph+ | Hydrea/ara-C/Vincristine/prednisone |
| B) Characteristics of Post-imatinib CML Samples | | | | | |
| 1 | 76 | M | BM | CP CHR, 100% Ph+ after imatinib | IFN-α/Hydrea imatinib (6 months) |
| 2 | 65 | M | BM | CP CHR, 95% Ph+ after imatinib | homoharringtonine + ara-C/FN-α imatinib (15 months) |
| 3 | 27 | M | BM | CP CHR and CCR after imatinib | IFN-α/Hydrea/imatinib (6 months) alloBMT |
| 4 | 54 | M | PB | AP CHR and 80% Ph+ after imatinib | IFN-α/Hydrea imatinib (6 months) |
| C) Characteristics of Imatinib resistant CML Samples | | | | | |
| 1. | 65 | F | PB | AP CHR, 100% Ph+ | IFN-α/Hydrea imatinib+/−FTI(2 months) |
| 2 | 74 | F | PB | AP Hematologic Relapse, 100% Ph+ | FN-α/Hydrea/imatinib + ara-C+ Hydrea (30 months) |
| 3 | 58 | M | PB | AP Hematologic Relapse, 100% Ph+ | Hydrea/alloBMT/imatinib (21 months) |
| 4 | 43 | M | BM | AP CHR, 100% Ph+ clonal evolution, trisomy 8 | IFN-α/Hydrea/alloBMT |
| 5 | 62 | M | BM | a) AP Hematologic Relapse, 100% Ph+ | IFN-α/Hydrea imatinib + arsenic |

BM = bone marrow;
PB = peripheral blood;
CP = chronic phase;
AP = accelerated phase;
BC = blast crisis;
Ph+ = Philadelphia chromosome positive;
CHR = complete hematologic remission;
FTI = farnesyl transferfase inhibitor;
allloBMT = allogeneic bone marrow transplant;
IFN-α = interferon alpha;
ara-C = cytosine arabinoside Isolation of Hematopoietic Stem Cell and Myeloid Progenitor Populations. Hematopoietic stem cells (HSC; $CD34^+CD38^-CD90$ $(Thy1)^+Lin^-$ cells) and myeloid progenitors including common myeloid progenitors (CMP; $CD34^+CD38^+IL-3R\alpha^+CD45RA^-$), granulocyte/macrophage progenitors (GMP; $CD34^+CD38^+IL-3R\alpha^+CD45RA^+$) and megakaryocyte/erythroid progenitors (MEP; $CD34^+CD38^+IL-3R\alpha^-CD45RA^-$) were isolated by FACS from normal and CML mononuclear cells as described previously.

Colony Forming Cell Assays. Colony forming cell (CFC) assays were performed as described previously. In replating experiments, individual colonies were plucked on day 14, replated in 96-well plates, and scored 14 days later. In some experiments, lentiviral constructs containing a LEF/TCF-GFP reporter, phosphoglycerate kinase (PGK) promoter-β-catenin-IRES-GFP or PGK-axin-IRES-GFP were added to CFC assays (LEF is lymphoid enhancer factor, TCF is T cell factor, GFP is green fluorescent protein, IRES is an internal ribosome entry site in viral RNA)

Quantitative Reverse Transcriptase-PCR for BCR-ABL expression. RNA isolated from 40 to 300 normal or CML hematopoietic stem cells, common myeloid progenitors, granulocyte/macrophage progenitors or megakaryocyte/erythroid progenitors (chronic phase, n=4; accelerated phase, n=7; blast crisis, n=3; post-imatinib, n=4; imatinib resistant, n=5) and quantitative reverse transcriptase-PCR analysis of BCR-ABL, β-catenin, LEF-1 and HPRT expression was performed as described.

β-catenin FACS Analysis. FACS-separated hematopoietic stem cells, common myeloid progenitors, granulocyte/macrophage progenitors, and megakaryocyte/erythroid progenitors were fixed with 0.8% paraformaldehyde and made permeable with 0.3% saponin. Cells were stained overnight with a fluorescein isothiocyanate (FITC)-conjugated antibody to β-catenin (Transduction Laboratories) or IgG$_1$ isotype control-FITC antibody, washed, and analyzed by FACS.

Confocal Fluorescence Microscopy. Normal (n=6) or CML hematopoietic stem cells or granulocyte/macrophage progenitors were FACS sorted onto glass slides, stained with anti-human CD45-FITC antibody, fixed in 4% paraformaldehyde followed by staining with a mouse monoclonal antibody to activated β-catenin (clone 8E4; Upstate, Lake Placid, N.Y.) at a dilution of 1/200 (2.5 μg/mL) and detected with an alexa 594-conjugated goat anti-mouse antibody as described previously. Hoechst 33342 (Molecular Probes) was used as a nuclear stain. Confocal images were obtained with a dual photon Zeiss LSM510 confocal fluorescence microscope at 100x magnification with the aid of Volocity™ software.

Figure 6:
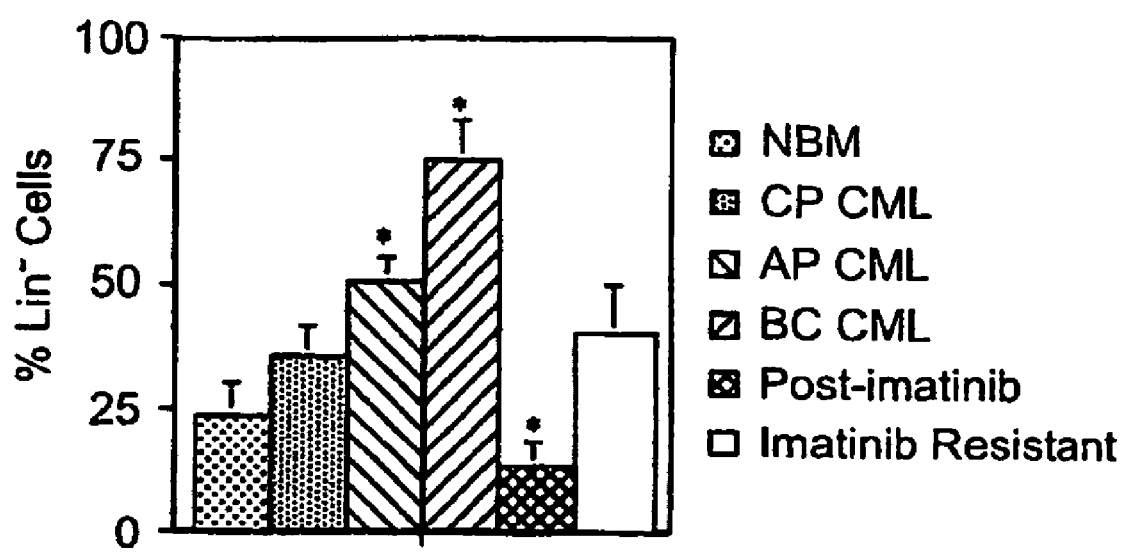
FIG. 6. A) The average percentage of $CD34^+$ cells in the lineage negative fraction (±S.E.M.) from normal bone marrow (n=11) versus chronic phase CML (n=5), accelerated phase CML (n=6, P<0.05), blast crisis CML (n=4, P<0.05), post-imatinib CML (n=6, P<0.05) and imatinib resistant CML (n=4) samples. B) Typical myeloid progenitor profiles, gated on CD34$^+$CD38$^+$Lin$^-$ cells, from normal bone marrow, chronic phase CML, accelerated phase CML and blast crisis CML. C) Myeloid progenitor profiles, gated on CD34$^+$CD38$^+$Lin$^-$ cells, from pre and post-imatinib CML samples.

LEF/TCF Reporter Assay. A lentiviral LEF/TCF reporter (FIG. 6) was used to assay β-catenin activation of LEF/TCF-mediated transcription in sorted normal and CML hematopoietic stem cell and myeloid progenitor populations, essentially as previously described with substitution of human cytokines IL-6 (10 ng/ml), Flt3 ligand (50 ng/ml), steel factor (SLF; 50 ng/ml) and thrombopoietin (10 ng/ml).

Lentiviral Transduction with LEF/TCF-GFP, PGK-β-catenin-IRES-GFP or PGK-Axin-IRES-GFP. Individual colonies were plucked into 50 microliters of myelocult media (H5100, Stem Cell Technologies), gently vortexed and resuspended in methylcellulose (150 microliters) supplemented with human cytokines including stem cell factor (SCF, 10 ng/ml); Flt3 ligand (FL, 10 ng/ml), IL-3 (20 ng/ml), IL-6 (10 ng/ml), IL-11 (10 ng/ml), thrombopoietin (TPO, 50 ng/ml); and erythropoietin (EPO, 4 units/ml) as previously described with or without lentiviral vectors containing LEF/TCF-GFP, phosphoglycerate kinase-β-catenin-IRES-GFP, phosphoglycerate kinase-Axin-IRES-GFP or a phosphoglycerate kinase-IRES-GFP control vector as previously described and cultured in 96 well plates (Falcon) for 14 days in a humidified 37° C. 5% $CO_2$ incubator. Colonies were scored on day 14 and GFP fluorescence was analyzed using a Zeiss inverted fluorescence microscope and photomicrographs were obtained at 40x magnification with the aid of SPOT software.

Quantitative RT-PCR for BCR-ABL, β-catenin and LEF-1. RNA was isolated from 40 to 300 normal or CML hematopoietic stem cells, common myeloid progenitors, granulocyte/macrophage progenitors, or megakaryocyte/erythroid progenitors. The BCR-ABL TaqMan quantitative RT-PCR reaction was performed with P210 BCR-ABL specific primers and a P210 BCR-ABL probe as previously described[49]. The quantitative RT-PCR assay for .beta.-catenin, LEF-1 and HPRT (as a control) was performed using SYBR Green core PCR reagents (Applied Biosystems) and sequence-specific primers (see below) with specific primers including:

on total RNA, isolated using the RNeasy Mini kit (Qiagen), that was reverse transcribed for 50 min at 42° C. using Oligo (dT) primers and Superscript™ II reverse transcriptase (Invitrogen). Amplification was performed with 50 cycles of two-step PCR (15 s at 95° C. and 60 s at 60° C.) after initial denaturation (95° C. for 10 min) using an ABI Prism 7700 Sequence Detector System (Applied Biosystems). Amplification of HPRT mRNA as an endogenous control was used to standardize reactions across samples. To compare relative target gene expression in the different samples, we designated one of the normal (NL) bone marrow samples as a reference and expressed the averaged sample value as percentage of the reference value.

Confocal Fluorescence Microscopy. Normal (n=5) or CML (chronic phase; n=2, accelerated phase; n=3, blast crisis; n=4, post-imatinib; n=2, imatinib resistant; n=2) hematopoietic stem cells or granulocyte/macrophage progenitors were FACS sorted onto glass slides. Slides were washed for 5 min in PBS, stained with anti-human CD45-FITC antibody (Anti-Hle-1; BD) for 1 hr, washed in PBS, fixed in 4% paraformaldehyde, for 10 min, and washed for 5 min in PBS/0.1% Tween-20 (PBS-T). Non-specific antibody binding was blocked with 5% goat serum, 1% BSA, 1:100 Fcγ receptor antibody in PBS-T and PBS for 1 hr, followed by staining for 1 hr with a mouse monoclonal antibody to nuclear-β-catenin as described previously. Slides were then washed with PBS-T, stained with an Alexa 594-conjugated goat anti-mouse antibody, washed, incubated for 10 min with Hoechst 33342 (Molecular Probes), rinsed with PBS-T, covered with Prolong antifade (Molecular Probes) and a coverslip. Confocal images were obtained with a dual photon Zeiss LSM510 confocal fluorescence microscope at 100x magnification. Excitation and emission spectra were 543 nm and 565-615 nm, respectively for β-catenin-Alexa 594. To visualize Hoechst 33342, a dual photon laser system with a 776 nm excitation wavelength, a beam splitter and a band pass of 435-485 nm was used while the excitation wavelength for CD45-FITC was 488 nm. Three dimensional renderings of confocal images were made with Volocity™ software.

Results

Hematopoietic stem and progenitor cells in CML. FACS analysis revealed an expansion in the bone marrow of CD34$^+$ lineage negative (Lin$^-$) cells in the accelerated and blast crisis phases of CML, as compared with normal bone marrow (FIG. 6A). Within the CD34$^+$Lin$^-$ stem and progenitor pool, the hematopoietic stem cell compartment (CD34$^+$CD38$^-$ CD90$^+$ Lin$^-$) did not expand with disease progression (FIG. 1A). However, evaluation of individual myeloid progenitor populations (CD34$^+$CD38$^+$Lin$^-$) revealed that in comparison with normal bone marrow, increased numbers of megakaryocyte/erythroid progenitors (P<0.001) were present in chronic phase CML, common myeloid progenitors were increased in Table-US-0004

|  | Forward | Reverse |
| --- | --- | --- |
| β-catenin | SEQ ID NO: 6<br>5'AATCAGCTGGCCTGGTTTGA3' | SEQ ID NO: 7<br>5'GGCCAATCACAATGCAAGTTC3' |
| LEF-1 | SEQ ID NO: 8<br>5'CCAGAGCATCTTGCATCCAAA3' | SEQ ID NO: 9<br>5'TTGCGCATGACAGGCAAAT3' |
| HPRT | SEQ ID NO: 10<br>5'CGTCTTGCTCGAGATGTGATG3' | SEQ ID NO: 11<br>5'TTTATAGCCCCCCTTGAGCAC3' | accelerated phase CML (P=0.004), and granulocyte/macrophage progenitors were increased in marrow from patients in blast crisis (P=0.02). (FIG. 1B). In patients responding to imatinib, there was a significant decrease in the number of CD34+ Lin− cells (P=0.027) compared with normal marrow and the proportion of individual myeloid progenitors reverted to normal, while samples from imatinib-resistant CML had increased numbers of granulocyte/macrophage progenitors (FIGS. 6A and C).

Figure 3B:
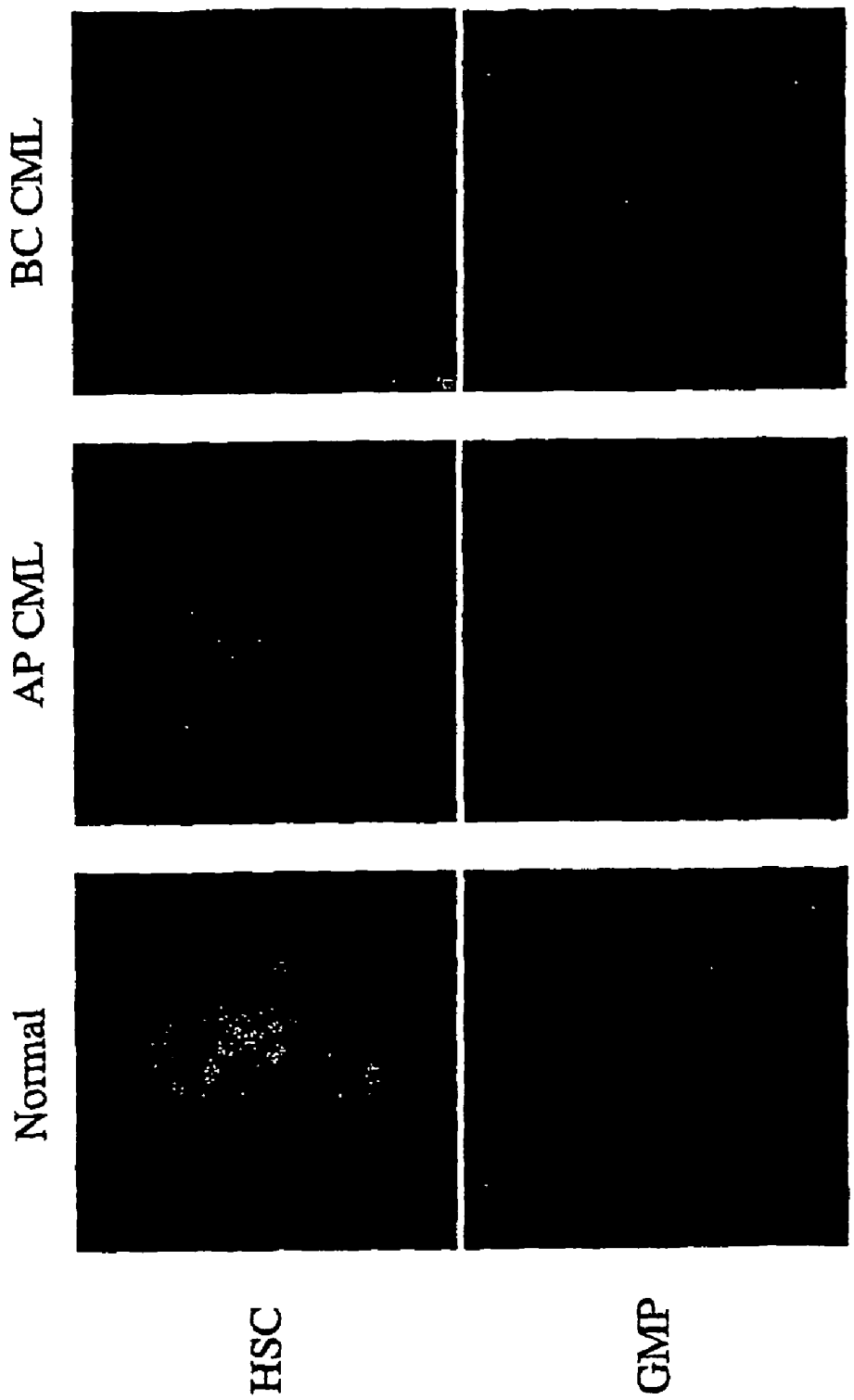
FIG. 3. A) Confocal fluorescence microscopic images of accelerated phase CML $CD34^+Lin^-$ cell stained with CD45 FITC (green); Hoechst, a blue nuclear stain; and activated β-catenin in red. B) β-catenin localization in normal (left; n=5), accelerated phase CML (center; n=3), and blast crisis CML (right; n=4) hematopoietic stem cells and granulocyte/macrophage progenitors. C) β-catenin localization in imatinib resistant CML hematopoietic stem cells (left; n=2), compared with imatinib resistant CML granulocyte/macrophage progenitors (center; n=2) or an isotype control (right; n=2). D) Histograms represent a percentage of maximal GFP fluorescence intensity (MFI) in the live cell gate. The histogram on the left represents LEF/TCF-GFP expression in normal (red) versus chronic phase CML hematopoietic stem cells (blue) while the histograms on the right are representative of LEF/TCF-GFP expression by normal (red) and blast crisis granulocyte/macrophage progenitors (blue) compared with untransduced blast crisis granulocyte/macrophage progenitors as a control (green).
Figure 3D:
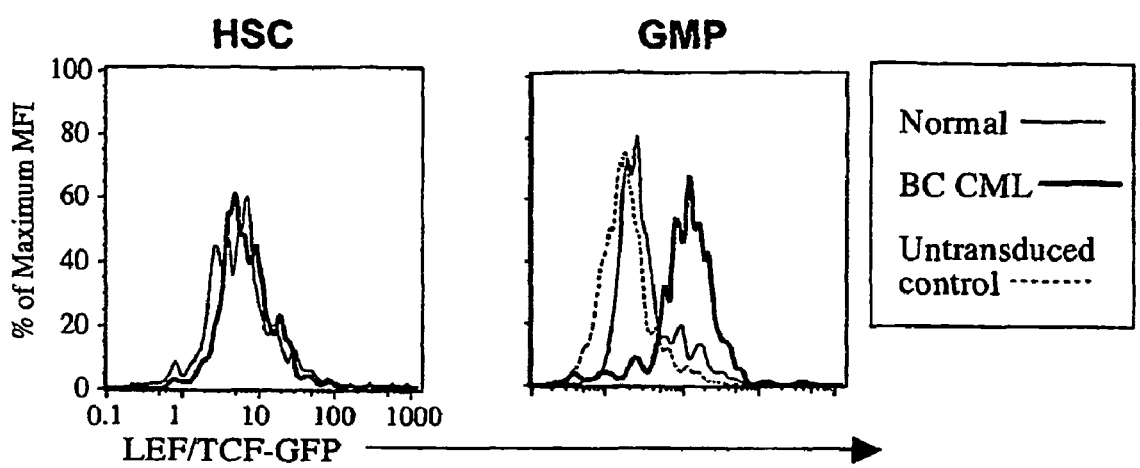
Figure 7:
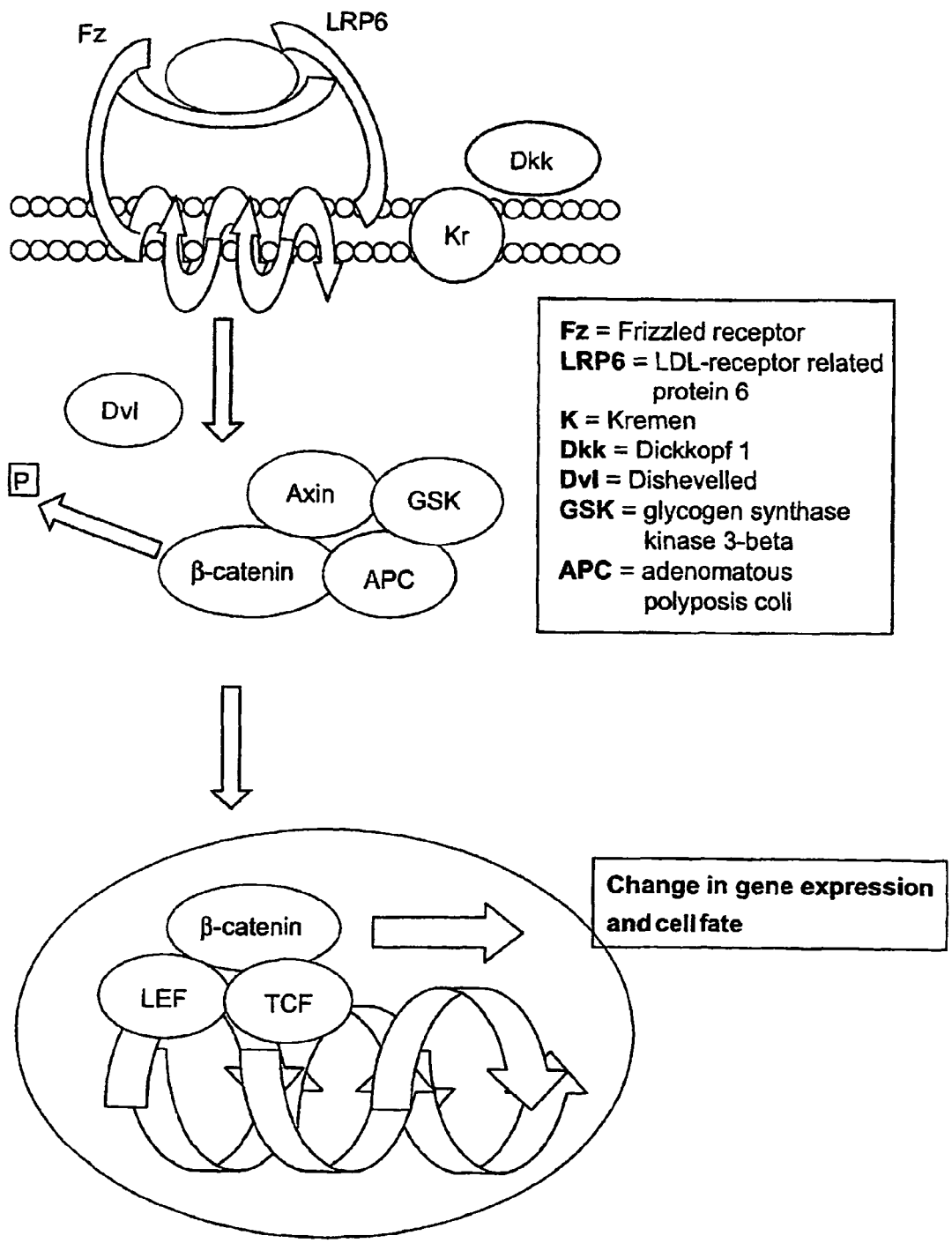
FIG. 7. Model of the canonical Wnt signaling pathway. In the absence of dickkopf 1 (Dkk)/Kremen (K) inhibition, LDL-receptor related protein 6 (LRP6) binds to the Wnt/Frizzled (Fz) complex and transduces a signal through dishevelled (Dvl) resulting in dephosphorylation of cytoplasmic β-catenin protein and dissociation from the axin/APC/GSK complex. Non-phosphorylated (activated or stabilized) β-catenin then translocates to the nucleus and binds to the LEF/TCF transcription factor complex where it mediates a change in gene expression and cell fate.
Figure 9:
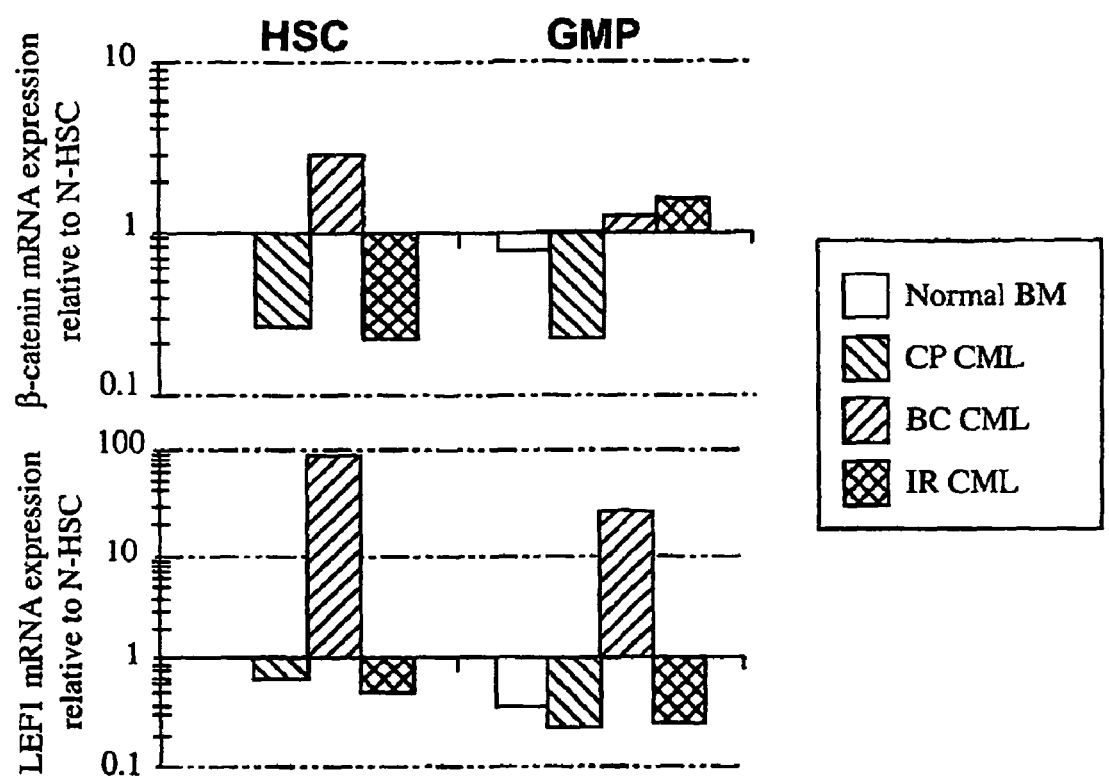
FIG. 9. β-catenin (upper panel) and LEF-1 (lower panel) transcript levels in hematopoietic stem cells or granulocyte/macrophage progenitors from normal bone marrow, or chronic phase, blast crisis or imatinib resistant CML patients. Transcript levels were internally controlled with HPRT, and shown relative to normal bone marrow hematopoietic stem cells.

Quantitative RT-PCR analysis demonstrated that in chronic phase CML, BCR-ABL transcripts were more abundant in hematopoietic stem cells than myeloid progenitors. Conversely, blast crisis was associated with increased BCR-ABL transcripts in myeloid progenitors, particularly common myeloid progenitors and granulocyte/macrophage progenitors (FIG. 1C). Because of the small numbers of progenitors we could obtain from banked samples, RT-PCR analysis for BCR-ABL was performed rather than fluorescence in situ hybridization. For this reason, we cannot exclude the possibility of a mixture of Ph+ and Ph− cells within the individual progenitor subsets.

β-Catenin activation in normal and leukemic stem and progenitor cells. FACS analysis revealed that total intracellular β-catenin levels were not significantly different in normal versus CML hematopoietic stem cells at any stage of CML (P=0.36 for chronic phase, P=0.30 for accelerated phase and P=0.33 for blast crisis). In contrast, myeloid progenitors from patients in accelerated phase (P=0.009) or blast crisis (P=0.04) had increased β-catenin levels compared with myeloid progenitors from normal donors (FIG. 2A). These levels were normal in patients who had received and responded to imatinib (FIG. 2B). Activated (non-phosphorylated) β-catenin-translocates to the nucleus (FIG. 7). Confocal fluorescence microscopy with monoclonal antibodies against non-phosphorylated β-catenin showed that the staining intensity of nuclear β-catenin was similar in normal, accelerated phase and blast crisis hematopoietic stem cells. However, there was a striking increase in activated β-catenin in granulocyte/macrophage progenitors from patients in blast crisis (FIG. 3B) or those patients who were resistant to imatinib, as compared with such progenitors from normal marrow (FIG. 3C). Concordantly, a LEF/TCF-GFP reporter assay, used to measure transcriptional activation by nuclear β-catenin, revealed similar levels of β-catenin/LEF/TCF-mediated transcriptional activation in normal, chronic phase and blast crisis hematopoietic stem cells, but an increase in granulocyte/macrophage progenitors from patients in blast crisis (FIG. 3D). Moreover, colonies derived from blast crisis CD34+Lin− cells that were transduced with the LEF/TCF-GFP reporter had high levels of β-catenin/LEF/TCF-mediated transcription as compared with their normal counterparts (FIG. 8). While normal granulocyte/macrophage progenitors express little β-catenin or its transcriptional co-activator, LEF-1, in the blast crisis and imatinib-resistant CML there is an increase in transcripts of both genes in such progenitors (FIG. 9), likely contributing to nuclear accumulation of β-catenin.

Figure 10:
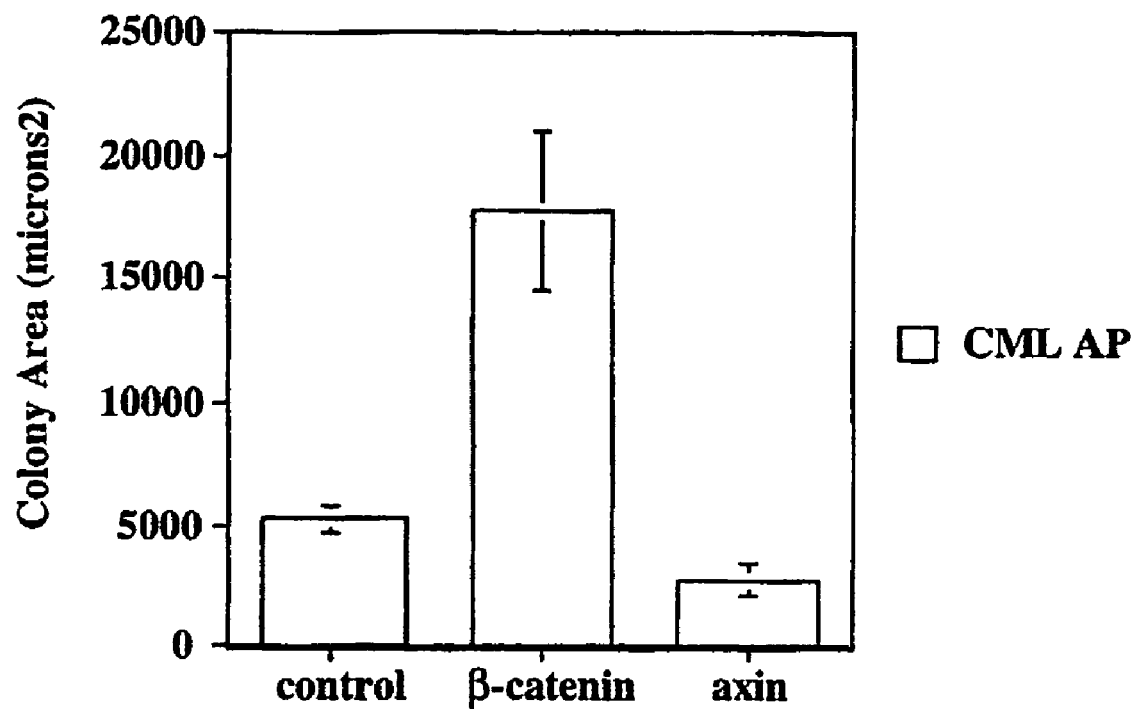
FIG. 10. Colony area (μm$^2$) of control accelerated phase CML colonies (left), compared with β-catenin (center) and axin (right) transduced colonies. Photomicrographs were obtained at 40× magnification with the aid of a Zeiss inverted microscope and Spot software which was also used to measure colony area.
Figure 11:
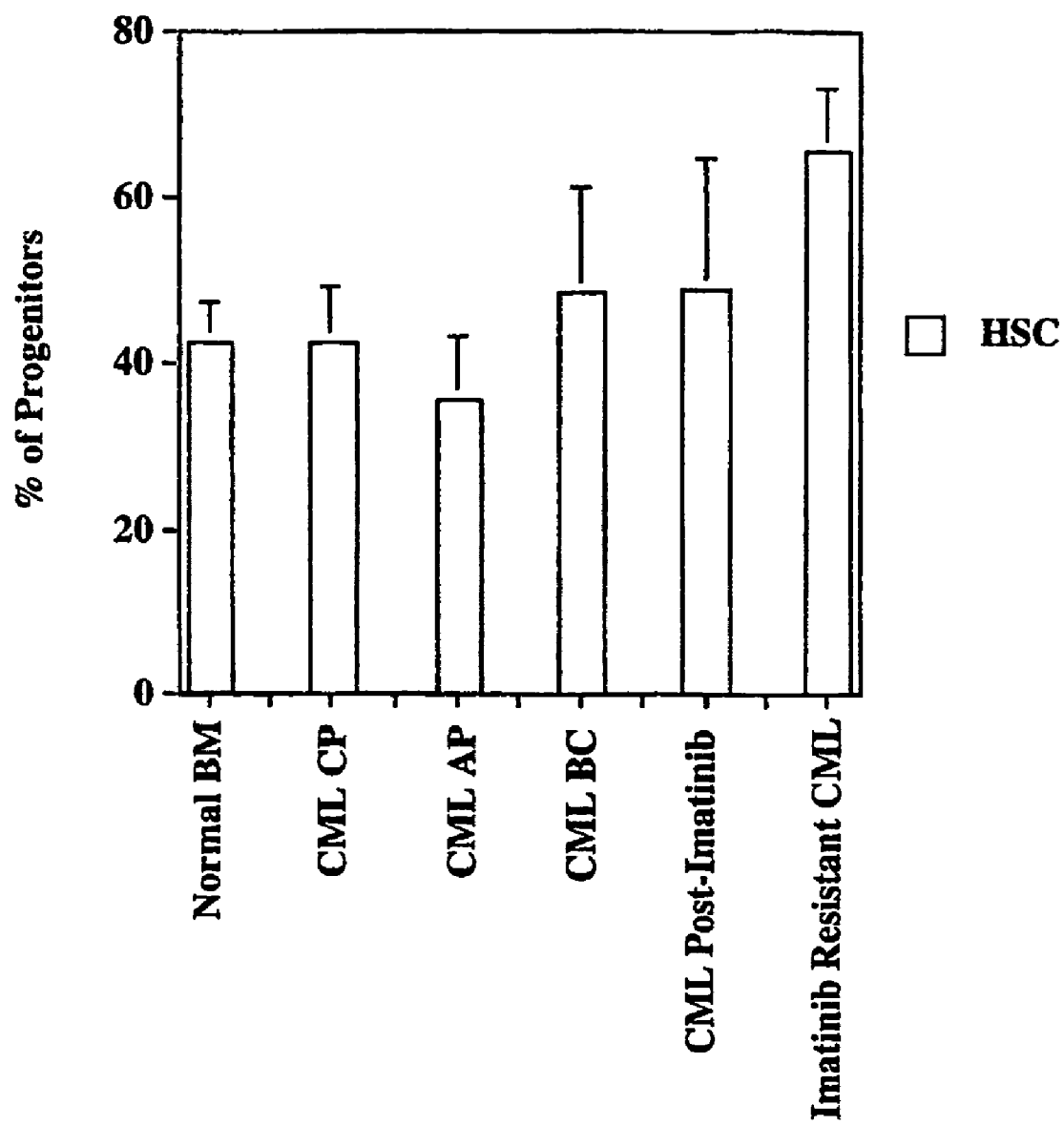
FIG. 11 is a graph depicting the expansion of hematopoietic stem cells in drug resistant CML.

CML granulocyte/macrophage progenitors self-renew in colony forming cell assays. We tested whether granulocyte/macrophage progenitors in CML gained the high proliferative potential and self-renewal capacity of hematopoietic stem cells as a result of β-catenin activation. CD34+Lin− cells from CML in the accelerated phase that were transduced with lentiviral β-catenin formed larger than normal colonies, whereas transduction of the cells with a β-catenin antagonist, axin, decreased colony size (FIG. 4A, FIG. 10 and FIG. 11). As shown in FIG. 11, effects can also been seen when the cells are tested with other wnt inhibitors.

In addition, enforced expression of β-catenin in normal granulocyte/macrophage progenitors conferred self-renewal capacity upon them in a replating assay (FIG. 4B). CML granulocyte/macrophage progenitors, but not normal granulocyte/macrophage progenitors, had a high replating capacity and retained the capacity to form myeloid colonies in colony forming cell assays (FIG. 4C). Finally, transduction of CML granulocyte/macrophage progenitors with axin, an inhibitor of β-catenin signaling, reduced replating capacity of leukemic cells (FIG. 4C, FIG. 10).

CML is believed to arise as a consequence of clonal expansion of hematopoietic stem cells that express the BCR-ABL fusion gene. However, recent work with transgenic mouse models of CML showed that while BCR-ABL is necessary for the development of a myeloproliferative syndrome resembling CML, hematopoietic stem cells need not be involved. Moreover, additional genetic or epigenetic events are required for progression to blast crisis. In man and mouse, hematopoietic stem cells are the only normal hematopoietic cells that self-renew, and therefore we have proposed that they are the only cells in the marrow that can accumulate preleukemic changes, whether by genetic or epigenetic means. However, it is also possible that a downstream progenitor can acquire self-renewal capacity. It is therefore critical to identify the population that contains leukemic stem cells in CML and other myeloid leukemias, and to identify events leading to progression of leukemia, the outcomes of these events, and the order of their appearance in leukemic stem cells and their precursors.

Here we show several unanticipated findings in CML: First, progression to blast crisis is associated with expansion of the myeloid progenitor fraction, which consists mainly of granulocyte/macrophage progenitors, rather than expansion of the hematopoietic stem cell pool. Second, BCR-ABL amplification occurs in granulocyte/macrophage progenitors, whereas BCR-ABL transcripts in hematopoietic stem cells remain relatively constant during progression of the disease. Third, the β-catenin pathway is activated in granulocyte/macrophage progenitors from patients in the accelerated phase, blast crisis, or who are resistant to imatinib. Fourth, granulocyte/macrophage progenitors in CML have self-renewal capacity. Five, β-catenin-mediated granulocyte/macrophage progenitor self-renewal in CML are inhibited by enforced expression of axin—a potent and highly specific β-catenin antagonist.

Figure 5:
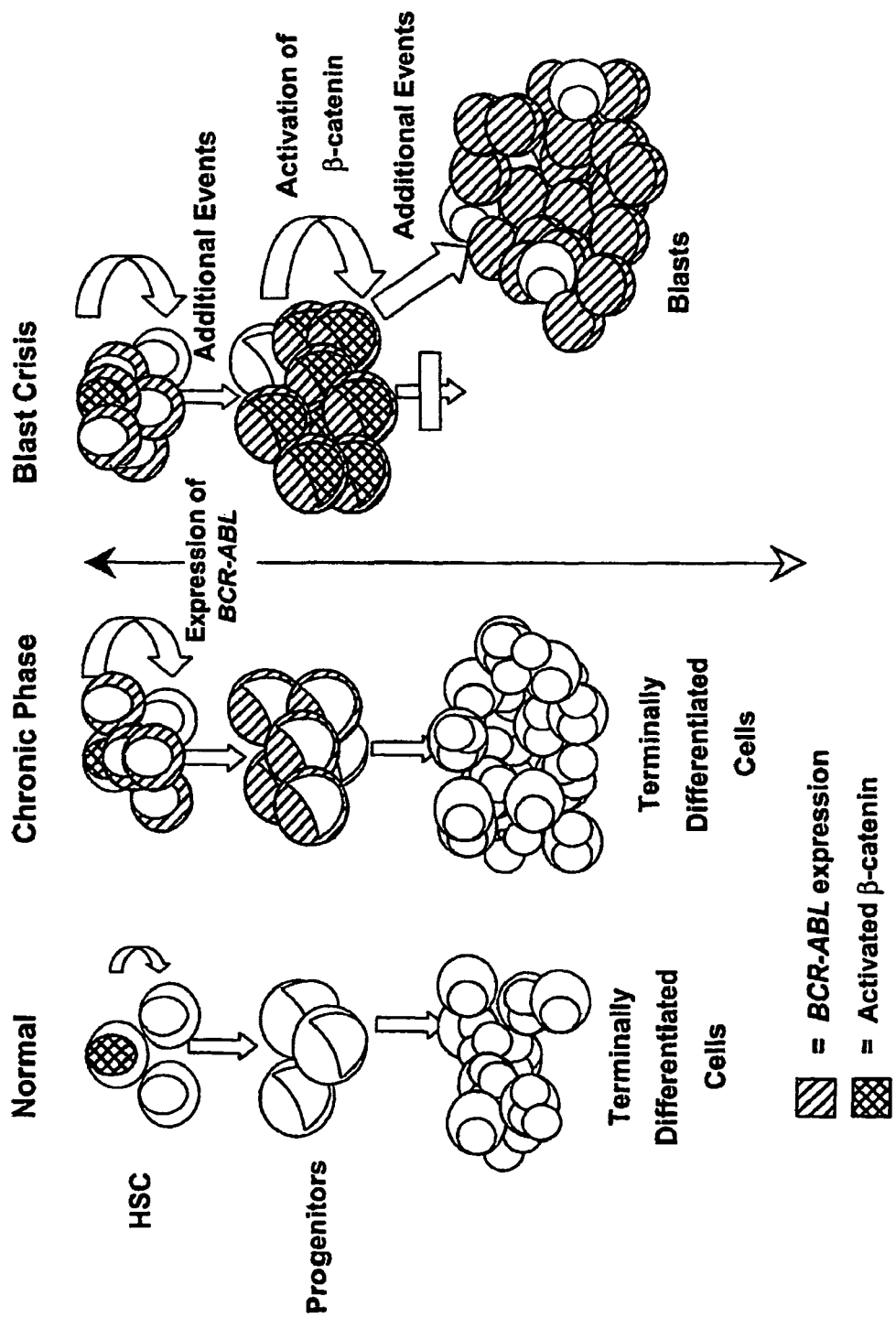
FIG. 5. Model of the Role of Activated β-catenin in CML Progression. In chronic phase CML, cells within the hematopoietic stem cell population have increased proliferative capacity secondary to elevated BCR-ABL expression, leading to a myeloproliferative syndrome, but cell death and differentiation pathways remain intact. Progression to blast crisis results from additional events, including activation of β-catenin in the granulocyte/macrophage progenitor population, leading to their higher proliferative and self-renewal capacity, possibly allowing them to become leukemia stem cells (LSC). Further events including avoidance of cell death, evasion of innate and adaptive immune responses, and a block in differentiation must occur for CML progression.

In chronic phase CML, hematopoietic stem cells and their progeny have an increased rate of proliferationdue to expression of the BCR-ABL fusion gene. This proliferation causes a myeloproliferative syndrome, but cell-death (apoptosis) and differentiation pathways remain intact. Progression of CML to blast crisis likely involves several events: BCR-ABL amplification, acquisition of resistance to apoptosis, genomic instability, escape from innate and adaptive immune responses, and activation of β-catenin, resulting in acquisition of self-renewal capacity by the granulocyte/macrophage progenitor population (FIG. 5). The activation of self-renewal via β-catenin in granulocyte/macrophage progenitors, which normally have no self-renewing capacity, may not only lead to expansion of the granulocyte/macrophage progenitor pool but also play a role in the production of blasts that occurs in advanced phases of CML.

The blast crises in this study were of the myeloid variety, the blast cells expressing myeloid lineage markers that are characteristic of stages between GM progenitors and their granulocyte/macrophage progeny. We expect that such blasts are more mature than GMP, and less mature than granulocytes and monocytes.

The cause of β-catenin activation in chronic myelogenous leukemia is unknown, and whether β-catenin or other components of the Wnt signaling pathway and p210$^{BCR-ABL}$ interact directly has yet to be determined. Targets of transcriptional activation by β-catenin/LEF-1 signaling include cyclin D1 and c-myc. Activation of transcription of cyclin D1 and c-myc has been reported to play a critical role in Abl, a Src-family kinase proto-oncogene, and BCR-ABL-mediated transformation and thus, cyclin D1 and c-myc may provide a final common pathway between BCR-ABL and β-catenin leading to CML progression. Additional Src-family kinase family members have also been shown to augment β-catenin activation. Other proto-oncogenes and tumor suppressors such as bmi-1, HOXB4 and notch also play a role in self-renewal of hematopoietic stem cells and may interact with β-catenin during leukemogenesis. Detection of activated β-catenin in highly purified CML progenitors may be used to predict progression, relapse, or development of imatinib resistance. Moreover, Wnt signaling pathway components, especially if mutated, provide targets for the development of molecular and/or immune therapies for CML.

Example 4

In order to track the long term leukemic potential of various progenitor subsets, progenitor cells were isolated from a human CML blast crisis, imatimib resistant patient, cell sorting and transduction protocols as described above. Cells were transduced with a lentiviral vector expressing luciferase-GFP as a marker. The cells were transplanted into RAG2$^{-/-}$ γ$_c$$^{-/-}$ mice as follows: HSC at 15×10$^3$ cells; CMP at 10$^4$ cells; total CD34$^+$CD38$^+$ at 90×10$^3$ cells. The number of marked cells was assessed in the viable mouse host through a fluorescent camera.

Figure 12:
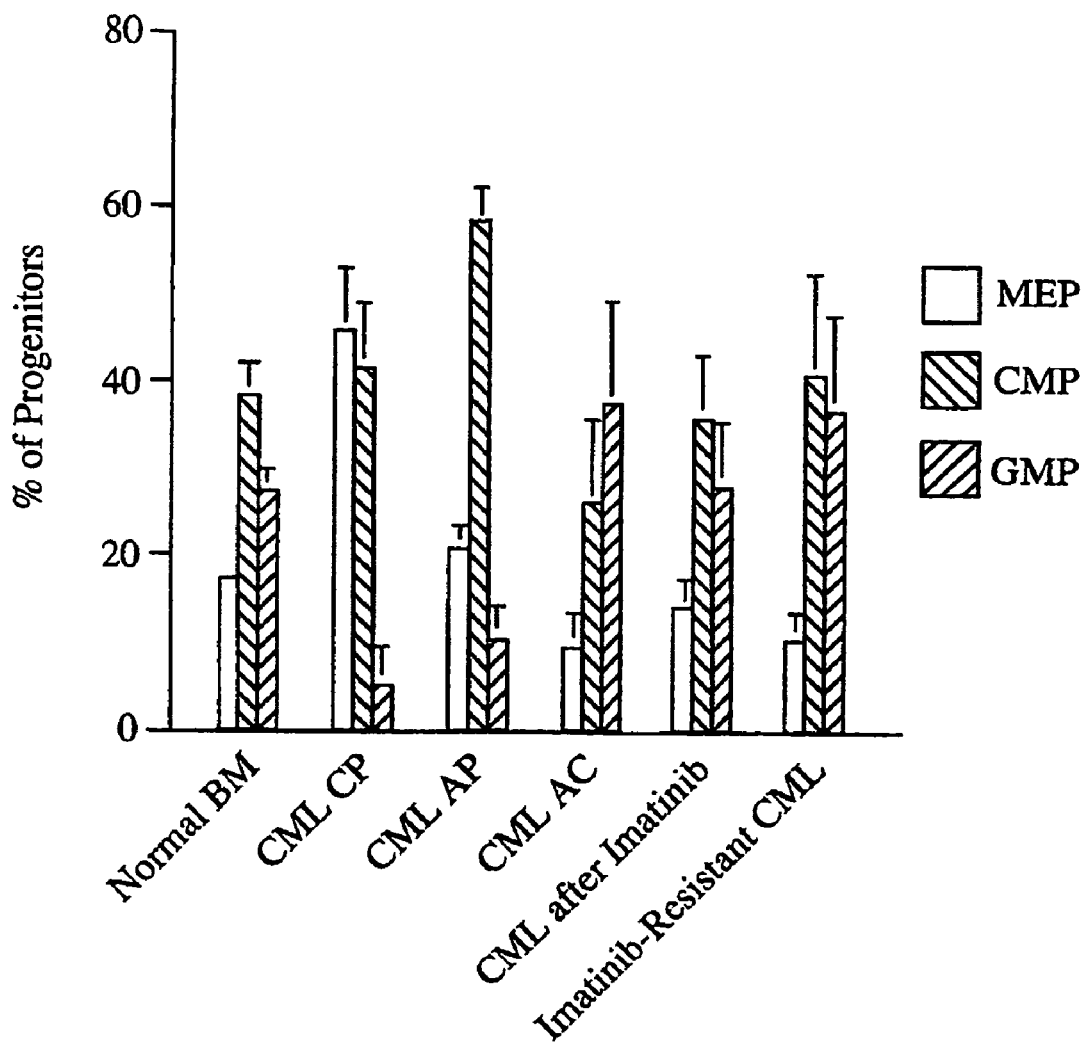
FIG. 12 depicts the characteristic myeloid progenitor profiles of CML chronic phase (CP); accelerated phase (AP); blast crisis (BC); post-treatment; and drug resistant phase.
Figure 13:
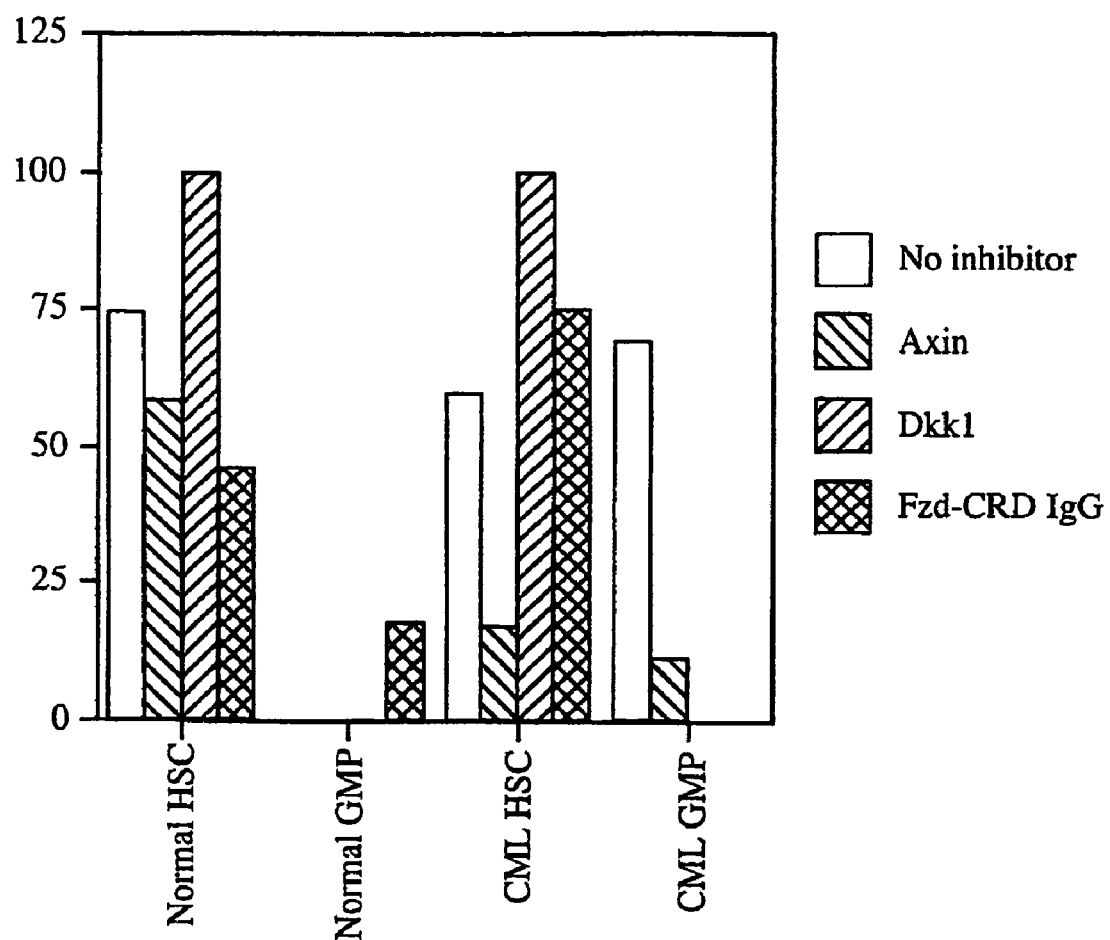
FIG. 13. Comparison of the effect of Wnt inhibitors on normal HSC and GMP; and CML patient HSC and GMP.
Figure 15:
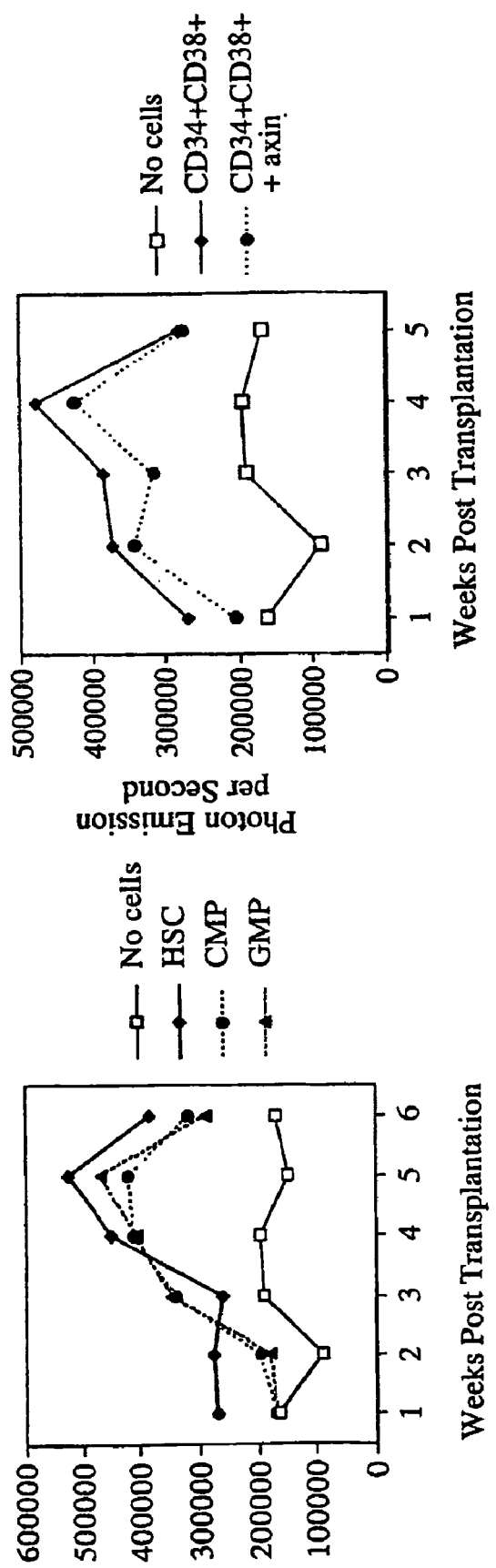
FIG. 15. Kinetics of CML progenitor engraftment.

A sample data point is shown in FIG. 12. The animals display regions of high concentration of the transduced cells. As shown in FIG. 13, the kinetics of engraftment can be readily followed in an animal using this method. The ability to trace engraftment without sacrificing the animal allows for accurate monitoring in vivo over an extended period of time.

What is claimed is:

1. A method of selecting for human leukemia stem cells (LSC), the method comprising:
   combining reagents that specifically recognize Thy-1, IL-7Rα (CD127), a lineage panel that distinguishes progenitor cells from lineage committed cells, and one or more reagents selected from a reagent that specifically recognizes IL3Rα, a reagent that specifically recognizes CD45RA, a reagent that specifically recognizes CD47 and a reagent that specifically recognizes Flk2 with a blood sample from a human leukemia patient; and
   selecting for cells that are Thy-1$^-$, IL-7Rα (CD127)$^-$, lineage panel$^-$, and one or more of IL-3Rα$^+$, CD45RA$^+$, CD47$^+$ and Flk2$^+$, to provide a population of leukemia stem cells having self-renewal capacity.

2. The method according to claim 1, wherein said leukemia is a myeloid leukemia.

3. The method according to claim 1, wherein said myeloid leukemia is CML or CMML.

4. The method of claim 1, comprising:
   combining said blood sample with a reagent that specifically recognizes IL3Rα; and
   selecting for cells that are IL3Rα$^+$.

5. The method of claim 1, comprising:
   combining said blood sample with a reagent that specifically recognizes CD45RA; and
   selecting for cells that are CD45RA$^+$.

6. The method of claim 1, wherein the leukemia stem cells have an activated β-catenin pathway that is inhibited with axin.

7. The method of claim 1, comprising:
   combining said blood sample with a reagent that specifically recognizes CD47; and
   selecting for cells that are CD47$^+$.

8. The method of claim 1, comprising:
   combining said blood sample with a reagent that specifically recognizes Flk2; and
   selecting for cells that are Flk2$^+$.

9. The method of claim 1 wherein said selecting is performed by flow cytometry.

10. The method of any of claim 1, 2, 3 or 4-9 wherein at least one reagent is an antibody.

11. The method of claim 9 wherein the antibody is labeled for direct detection.

12. The method of claim 7 wherein the reagent that specifically recognizes CD47 is an antibody.

13. The method of claim 12 wherein the antibody is labeled for direct detection.

14. The method of claim 7, wherein said leukemia is CML or CMML.

* * * * *